US010853451B2

(12) United States Patent
Rowe et al.

(10) Patent No.: US 10,853,451 B2
(45) Date of Patent: Dec. 1, 2020

(54) DRUG FORMULARY APPLICATION

(71) Applicant: TIMELESS VETERINARY SYSTEMS INC., Charlottetown (CA)

(72) Inventors: John L. Rowe, Charlottetown (CA); Brad D. Pineau, Stratford (CA)

(73) Assignee: TIMELESS VETERINARY SYSTEMS INTERNATIONAL LIMITED, Hamilton (BM)

( * ) Notice: Subject to any disclaimer, the term of this patent is extended or adjusted under 35 U.S.C. 154(b) by 1171 days.

(21) Appl. No.: 14/896,267

(22) PCT Filed: Jun. 6, 2014

(86) PCT No.: PCT/CA2014/000489
§ 371 (c)(1),
(2) Date: Dec. 4, 2015

(87) PCT Pub. No.: WO2014/194410
PCT Pub. Date: Dec. 11, 2014

(65) Prior Publication Data
US 2016/0125146 A1   May 5, 2016

Related U.S. Application Data

(60) Provisional application No. 61/831,975, filed on Jun. 6, 2013.

(51) Int. Cl.
*G06F 19/00* (2018.01)
(52) U.S. Cl.
CPC .......... *G06F 19/326* (2013.01); *G06F 19/325* (2013.01); *G06F 19/3456* (2013.01); *G06F 19/3468* (2013.01)
(58) Field of Classification Search
CPC combination set(s) only.
See application file for complete search history.

(56) References Cited

U.S. PATENT DOCUMENTS

| 6,081,786 A | 6/2000 | Barry et al. |
| 7,067,437 B2 | 7/2006 | Levy |

(Continued)

FOREIGN PATENT DOCUMENTS

WO   WO 2009/026938   3/2009

OTHER PUBLICATIONS

Flannigan et al., "Students Prescribing Emergency Drug Infusions Utilising Smartphones Outperform Consultants Using BNFCs",Resuscitation, vol. 82, No. 11, Nov. 2011, pp. 1424-1427.

(Continued)

*Primary Examiner* — Michael Tomaszewski
*Assistant Examiner* — William T. Monticello
(74) *Attorney, Agent, or Firm* — Norton Rose Fulbright Canada LLP

(57) ABSTRACT

A system and method for providing a treatment protocol. A memory stores drug data identifying a plurality of drugs, and, for each drug, at least one indication for the drug and a unit dose value of the drug to be administered for treating each indication, and evidence-based data indicative of an effectiveness of each drug for treating the at least one indication. Input data identifying a selected drug is received, the at least one indication for the selected drug determined, the unit dose value of the selected drug for the at least one indication and the evidence-based data for the selected drug retrieved from the memory, a measure of a level of confidence in the evidence-based data for the selected drug determined, and the at least one indication, the unit dose value, and the measure of the level of confidence output for the selected drug.

16 Claims, 24 Drawing Sheets

(56) References Cited

U.S. PATENT DOCUMENTS

| | | |
|---|---|---|
| 7,574,370 B2 | 8/2009 | Mayaud |
| 7,895,060 B1 | 2/2011 | Mahoney et al. |
| 7,991,485 B2 | 8/2011 | Zakim |
| 8,055,511 B2 | 11/2011 | McCallie et al. |
| 8,145,590 B2 | 3/2012 | Brockway et al. |
| 8,165,897 B2 | 4/2012 | Beraja et al. |
| 2003/0204415 A1 | 10/2003 | Knowlton |
| 2004/0172285 A1 | 9/2004 | Gibson |
| 2006/0089545 A1 | 4/2006 | Ratjen et al. |
| 2006/0129357 A1* | 6/2006 | Francis et al. |
| 2006/0258985 A1* | 11/2006 | Russell |
| 2008/0082503 A1* | 4/2008 | Jung et al. |
| 2008/0249374 A1 | 10/2008 | Morita et al. |
| 2009/0171697 A1* | 6/2009 | Glauser et al. |
| 2009/0281835 A1* | 11/2009 | Patwardhan et al. |
| 2009/0306944 A1 | 12/2009 | Willmann et al. |
| 2009/0319300 A1 | 12/2009 | Manakkil |
| 2010/0312580 A1 | 12/2010 | Tarassenko et al. |
| 2011/0004189 A1* | 1/2011 | Vaidya et al. |
| 2011/0276347 A1* | 11/2011 | Dalton |
| 2012/0191466 A1 | 7/2012 | Quint et al. |
| 2012/0239410 A1 | 9/2012 | Bergstrom et al. |
| 2012/0301864 A1 | 11/2012 | Bagchi et al. |
| 2013/0041683 A1* | 2/2013 | Boissel |
| 2013/0268290 A1* | 10/2013 | Jackson et al. |
| 2015/0363559 A1* | 12/2015 | Jackson et al. |

OTHER PUBLICATIONS

Brouwer et al., "Computerized Drug Therapy: Application of the Hand-Held Microcomputer to Dosage Regimen Design", International Journal of Bio-medical Computing, vol. 17, No. 1, Aug. 1985, pp. 49-55.

Anokwa et al., "Design of a Phone-Based Clinical Decision Support System for Resource-Limited Settings", pp. 1-12.

\* cited by examiner

DRUG FORMULARY APPLICATION

CROSS-REFERENCE TO RELATED APPLICATIONS

This patent application claims priority of U.S. provisional Application Ser. No. 61/831,975, filed on Jun. 6, 2013, the contents of which are hereby incorporated.

TECHNICAL FIELD

The present invention relates to the field of drug formulary applications.

BACKGROUND OF THE ART

Clinicians typically decide on medication to prescribe to a patient on the basis of information they have memorized or can rapidly look up in a reference guide. In particular, clinicians may use drug formularies to obtain information about particular medications approved to be prescribed for a given condition. Drug formularies may also provide additional clinical information, such as drug dosages, side effects, and contraindications.

Drug formularies may be provided using suitable computerized systems. In order to be provided the information he/she is seeking, the user is typically prompted to enter data via a suitable interface. However, a high level of input is usually required from the user prior to outputting the desired drug information. In addition, the user often needs to access external sources in order to be able to provide the requested input data. Such data entry can therefore prove cumbersome and disadvantageous as it can constrain the time of a medical professional. Moreover, such drug formulary systems typically fail to provide a means for assessing the relevance of the information output to the user.

There is therefore a need to improve on existing drug formularies.

SUMMARY

In accordance with a first broad aspect, there is described a system for providing a treatment protocol, the system comprising a memory having stored therein drug data identifying a plurality of drugs, and, for each one of the plurality of drugs, at least one indication for the drug and a unit dose value of the drug to be administered for treating each of the at least one indication, and evidence-based data indicative of an effectiveness of each one of the plurality of drugs for treating the at least one indication. The system further comprises a processor and at least one application stored in the memory and executable by the processor for receiving input data identifying a selected one of the plurality of drugs, determining the at least one indication for the selected drug, retrieving from the memory the unit dose value of the selected drug for the at least one indication, retrieving from the memory the evidence-based data for the selected drug, determining a measure of a level of confidence in the evidence-based data for the selected drug, and outputting, for the selected drug, the at least one indication, the unit dose value, and the measure of the level of confidence.

In some embodiments, the memory has stored therein one or more attributes for the evidence-based data, the one or more attributes comprising at least one of a type of the evidence-based data, a type of blinding for the evidence-based data, a type of control for the evidence-based data, a randomization for the evidence-based data, a sample group size for the evidence-based data, a number of trials for the evidence-based data, and an assessment of whether an animal signalment is provided in the evidence-based data.

In some embodiments, the memory has stored therein a plurality of ranking levels indicative of the level of confidence in the evidence-based data, each ranking level determined on the basis of the one or more attributes of the evidence-based data and associated with a combination of the one or more attributes, and further wherein the at least one application is executable by the processor for receiving the input data indicative of a given one of the at least one indication for which the selected drug is to be administered, and determining the measure of the level of confidence in the evidence-based data indicative of the effectiveness of the selected drug for treating the given indication comprising retrieving the plurality of ranking levels from the memory and correlating the one or more attributes of the evidence-based data for the selected drug with the plurality of ranking levels for attributing a selected one of the plurality of ranking levels to the evidence-based data for the selected drug.

In some embodiments, the at least one application is executable by the processor for outputting the measure of the level of confidence as a visual scale indicative of the selected ranking level relative to the plurality of ranking levels.

In some embodiments, the at least one application is executable for outputting the evidence-based data for the selected drug.

In some embodiments, the at least one application is executable by the processor for receiving the input data indicative of a given one of the at least one indication affecting a patient, determining at least one calculation applicable for computing a total dosage of the selected drug to be administered to the patient for treating the given indication, performing the at least one calculation, and outputting the computed total dosage.

In some embodiments, the memory has stored therein calculation data associated with each one of the plurality of drugs, the calculation data indicative of at least one calculation applicable for computing the total dosage of each drug, and further wherein the at least one application is executable by the processor for receiving the input data comprising a weight of the patient, retrieving from the memory the calculation data, determining from the calculation data that the at least one calculation applicable for computing the total dosage of the selected drug for the given indication comprises multiplying the weight of the patient by the unit dose value of the selected drug for the given indication, and performing the at least one calculation accordingly.

In some embodiments, the memory has stored therein the drug data identifying one or more of the plurality of drugs to be administered by continuous rate infusion, the drug data comprising a recommended continuous rate infusion dosage for each one of the one or more of the plurality of drugs, and further wherein the at least one application is executable by the processor for determining from the drug data that the selected drug is among the one or more of the plurality of drugs to be administered by continuous rate infusion, retrieving the recommended constant rate infusion dosage for the selected drug from the memory, receiving the input data comprising a weight of the patient, a concentration of the selected drug, a volume of a fluid container for use in administering the selected drug, and a duration of administration of the selected drug, retrieving from the memory the calculation data, determining from the calculation data that the at least one calculation comprises computing a total volume of the selected drug to be added to the volume of the fluid container and a drip rate of the fluid container, performing the at least one calculation on the basis of the retrieved recommended constant rate infusion dosage and the input data, and outputting the computed total volume and drip rate.

In some embodiments, the at least one application is executable by the processor for receiving the input data comprising a height and a weight of the patient, retrieving from the memory the calculation data, determining from the calculation data that the at least one calculation comprises calculating, on the basis of the height and the weight, a body surface area of the patient and computing the total dosage for the selected drug on the basis of the calculated body surface area and the unit dose value of the selected drug for the given indication, and performing the at least one calculation accordingly.

In some embodiments, the memory has stored therein the drug data comprising one or more attributes of the plurality of drugs, the one or more attributes comprising, for each one of the plurality of drugs, at least one of a brand name of the drug, a generic name of the drug, a therapeutic class of the drug, a regional availability of the drug, a rate of administration of the drug, a mode of administration of the drug, a type of condition the drug is indicated for, advice for treating the condition using the drug, one or more contraindications of the drug, one or more effects from administration of the drug, one or more combination treatments to be used with the drug, one or more reversal agents for the drug, and one or more animal species the drug is indicated for treating, and further wherein the at least one application is executable by the processor for retrieving at least one of the one or more attributes for the selected drug from the memory and outputting the retrieved at least one of the one or more attributes.

In accordance with a second broad aspect, there is described a method for providing a treatment protocol, the method comprising receiving input data identifying a selected one of a plurality of drugs; determining at least one indication for the selected drug; retrieving a unit dose value of the selected drug for the at least one indication from a memory having stored therein drug data identifying the plurality of drugs, and, for each one of the plurality of drugs, the at least one indication for the drug and the unit dose value of the drug to be administered for treating each of the at least one indication, and evidence-based data indicative of an effectiveness of each one of the plurality of drugs for treating the at least one indication; retrieving from the memory the evidence-based data for the selected drug; determining a measure of a level of confidence in the evidence-based data for the selected drug; and outputting, for the selected drug, the at least one indication, the unit dose value, and the measure of the level of confidence.

In some embodiments, the method further comprises receiving the input data indicative of a given one of the at least one indication for which the selected drug is to be administered; and determining the measure of the level of confidence in the evidence-based data indicative of the effectiveness of the selected drug for treating the given indication comprising retrieving a plurality of ranking levels from the memory, the memory having stored therein one or more attributes for the evidence-based data and the plurality of ranking levels indicative of the level of confidence in the evidence-based data, each ranking level determined on the basis of the one or more attributes of the evidence-based data and associated with a combination of the one or more attributes, and correlating the one or more attributes of the evidence-based data for the selected drug with the plurality of ranking levels for attributing a selected one of the plurality of ranking levels to the evidence-based data for the selected drug.

In some embodiments, the measure of the level of confidence is output as a visual scale indicative of the selected ranking level relative to the plurality of ranking levels.

In some embodiments, the method further comprises outputting the evidence-based data for the selected drug.

In some embodiments, the received input data is indicative of a given one of the at least one indication affecting a patient, and further comprising determining at least one calculation applicable for computing a total dosage of the selected drug to be administered to the patient for treating the given indication, performing the at least one calculation, and outputting the computed total dosage.

In some embodiments, the method further comprises receiving the input data comprising a weight of the patient; retrieving from calculation data the memory, the memory having stored therein the calculation data associated with each one of the plurality of drugs, the calculation data indicative of at least one calculation applicable for computing the total dosage of each drug; determining from the calculation data that the at least one calculation applicable for computing the total dosage of the selected drug for the given indication comprises multiplying the weight of the patient by the unit dose value of the selected drug for the given indication; and performing the at least one calculation accordingly.

In some embodiments, the method further comprises determining from the drug data that the selected drug is among one or more of the plurality of drugs to be administered by continuous rate infusion; retrieving a recommended constant rate infusion dosage for the selected drug from the memory; receiving the input data comprising a weight of the patient, a concentration of the selected drug, a volume of a fluid container for use in administering the selected drug, and a duration of administration of the selected drug; retrieving from the calculation data the memory; determining from the calculation data that the at least one calculation comprises computing a total volume of the selected drug to be added to the volume of the fluid container and a drip rate of the fluid container; performing the at least one calculation on the basis of the retrieved recommended constant rate infusion dosage and the input data; and outputting the computed total volume and drip rate.

In some embodiments, the method further comprises receiving the input data comprising a height and a weight of the patient, retrieving the calculation data from the memory, determining from the calculation data that the at least one calculation comprises calculating, on the basis of the height and the weight, a body surface area of the patient and computing the total dosage for the selected drug on the basis of the calculated body surface area and the unit dose value of the selected drug for the given indication, and performing the at least one calculation accordingly.

In some embodiments, the method further comprises retrieving at least one of one or more attributes for the selected drug from the memory and outputting the retrieved at least one of the one or more attributes, the one or more attributes comprising, for each one of the plurality of drugs, at least one of a brand name of the drug, a generic name of the drug, a therapeutic class of the drug, a regional availability of the drug, a rate of administration of the drug, a mode of administration of the drug, a type of condition the drug is indicated for, advice for treating the condition using the drug, one or more contraindications of the drug, one or more effects from administration of the drug, one or more combination treatments to be used with the drug, one or more reversal agents for the drug, and one or more animal species the drug is indicated for treating.

In accordance with a third broad aspect, there is described a computer readable medium having stored thereon program code executable by a processor for providing a treatment protocol, the program code executable for receiving input data identifying a selected one of a plurality of drugs; determining at least one indication for the selected drug; retrieving a unit dose value of the selected drug for the at least one indication from a memory having stored therein drug data identifying the plurality of drugs, and, for each one of the plurality of drugs, the at least one indication for the drug and the unit dose value of the drug to be administered for treating each of the at least one indication, and evidence-based data indicative of an effectiveness of each one of the plurality of drugs for treating the at least one indication; retrieving from the memory the evidence-based data for the selected drug; determining a measure of a level of confidence in the evidence-based data for the selected drug; and outputting, for the selected drug, the at least one indication, the unit dose value, and the measure of the level of confidence.

BRIEF DESCRIPTION OF THE DRAWINGS

Further features and advantages of the present invention will become apparent from the following detailed description, taken in combination with the appended drawings, in which:

FIG. 2b is a block diagram of the calculator module of FIG. 2a;

FIG. 2c is a block diagram of the clinical guidance module of FIG. 2a;

It will be noted that throughout the appended drawings, like features are identified by like reference numerals.

DETAILED DESCRIPTION

Figure 1:
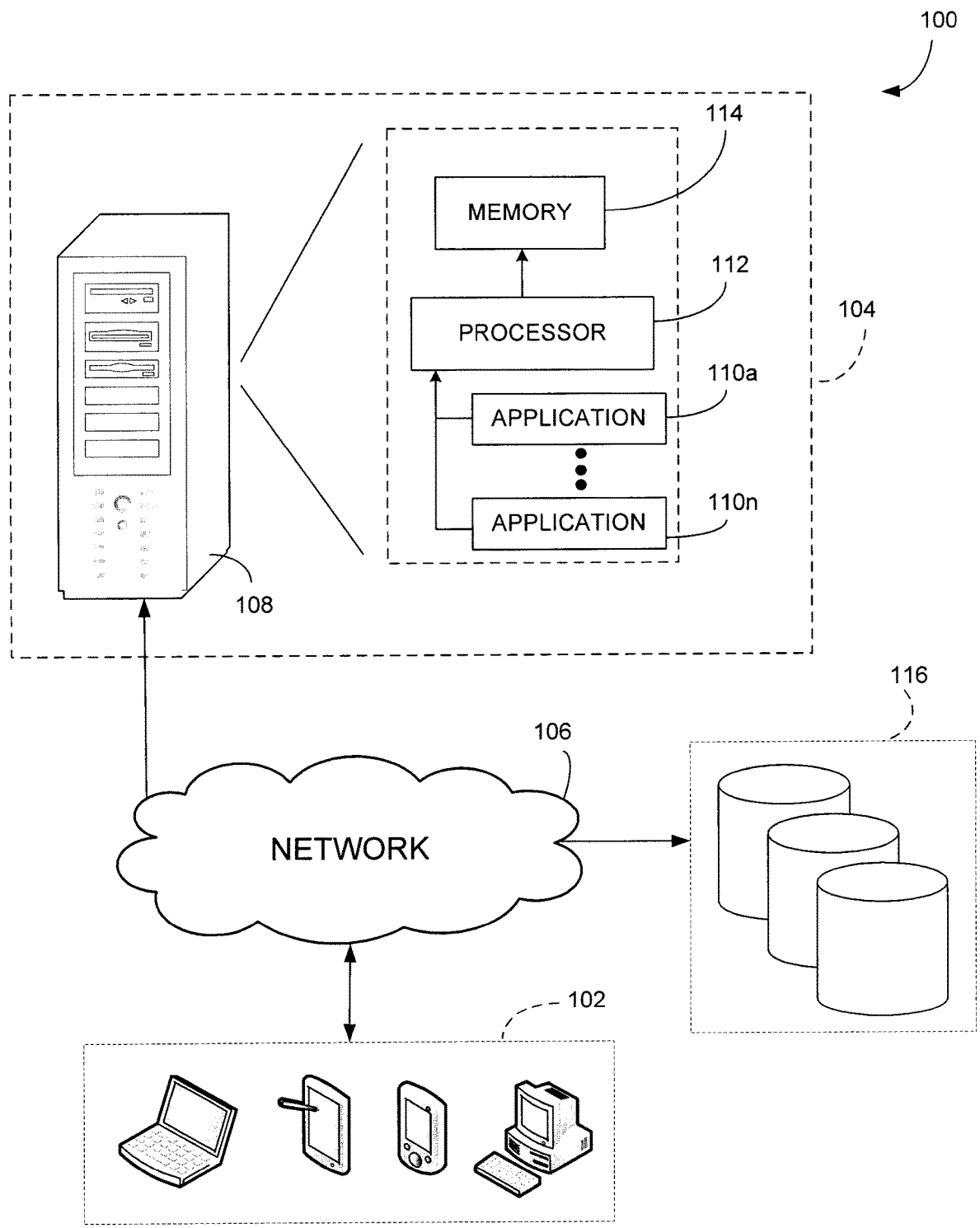
FIG. 1 is a block diagram illustrating a system for providing drug information, in accordance with an illustrative embodiment of the present invention.

Referring to FIG. 2, there is illustrated a system 100 for providing drug information in accordance with an illustrative embodiment of the present invention. The system 100 provides users with a drug dosage that is best suited to treat a given condition. The system 100 also provides other pertinent data, such as the most suitable rate of drug administration or drug therapy protocol. It should be understood that, although the system 100 is described herein as being used for veterinary medicine, the system 100 can be used for other applications, such as human medicine.

The system 100 comprises a plurality of devices as in 102 adapted to communicate with a drug formulary system 104 over a network 106. The devices 102 may comprise any device, such as a personal computer, a tablet computer, a personal digital assistant, a smart phone, or the like, which is configured to communicate over the network 106, such as the Internet, the Public Switch Telephone Network (PSTN), a cellular network, or others known to those skilled in the art. Although illustrated as being separate and remote from the devices 102, it should be understood that the drug formulary system 104 may also be integrated with the devices 102, either as a downloaded software application, a firmware application, or a combination thereof. It should also be understood that several devices as in 102 may access the drug formulary system 104 at once to obtain drug information therefrom.

The drug formulary system 104 illustratively comprises one or more server(s) accessible via the network 106. For example, a series of servers corresponding to a web server, an application server, and a database server may be used. These servers are all represented by server 108. The server 108 may be accessed by a user using one of the devices 102. The server 108 may comprise, amongst other things, a plurality of applications 110a . . . 110n running on a processor 112 coupled to a memory 114. It should be understood that while the applications 110a . . . 110n presented herein are illustrated and described as separate entities, they may be combined or separated in a variety of ways.

One or more databases 116 may be integrated directly into the memory 114 or may be provided separately therefrom and remotely from the server 108 (as illustrated). In the case of a remote access to the databases 116, access may occur via any type of network 106, as indicated above. The various databases 116 described herein may be provided as collections of data or information organized for rapid search and retrieval by a computer. The databases 116 may be structured to facilitate storage, retrieval, modification, and deletion of data in conjunction with various data-processing operations. The databases 116 may consist of a file or sets of files that can be broken down into records, each of which consists of one or more fields. Database information may be retrieved through queries using keywords and sorting commands, in order to rapidly search, rearrange, group, and select the field. The databases 116 may be any organization of data on a data storage medium, such as one or more servers.

In one embodiment, the databases 116 are secure web servers and Hypertext Transport Protocol Secure (HTTPS) capable of supporting Transport Layer Security (TLS), which is a protocol used for access to the data. Communications to and from the secure web servers may be secured using Secure Sockets Layer (SSL). Identity verification of a user may be performed using usernames and passwords for all users. Various levels of access rights may be provided to multiple levels of users.

Alternatively, any known communication protocols that enable devices within a computer network to exchange information may be used. Examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), SSH (Secure Shell Remote Protocol)

The memory 114 accessible by the processor 112 may receive and store data. The memory 114 may be a main memory, such as a high speed Random Access Memory (RAM), or an auxiliary storage unit, such as a hard disk, flash memory, or a magnetic tape drive. The memory 114 may be any other type of memory, such as a Read-Only Memory (ROM), Erasable Programmable Read-Only Memory (EPROM), or optical storage media such as a videodisc and a compact disc.

The processor 112 may access the memory 114 to retrieve data. The processor 112 may be any device that can perform operations on data. Examples are a central processing unit (CPU), a front-end processor, a microprocessor, and a network processor. The applications 110a . . . 110n are coupled to the processor 112 and configured to perform various tasks as explained below in more detail. An output may be transmitted to the devices 102.

Figure 2A:
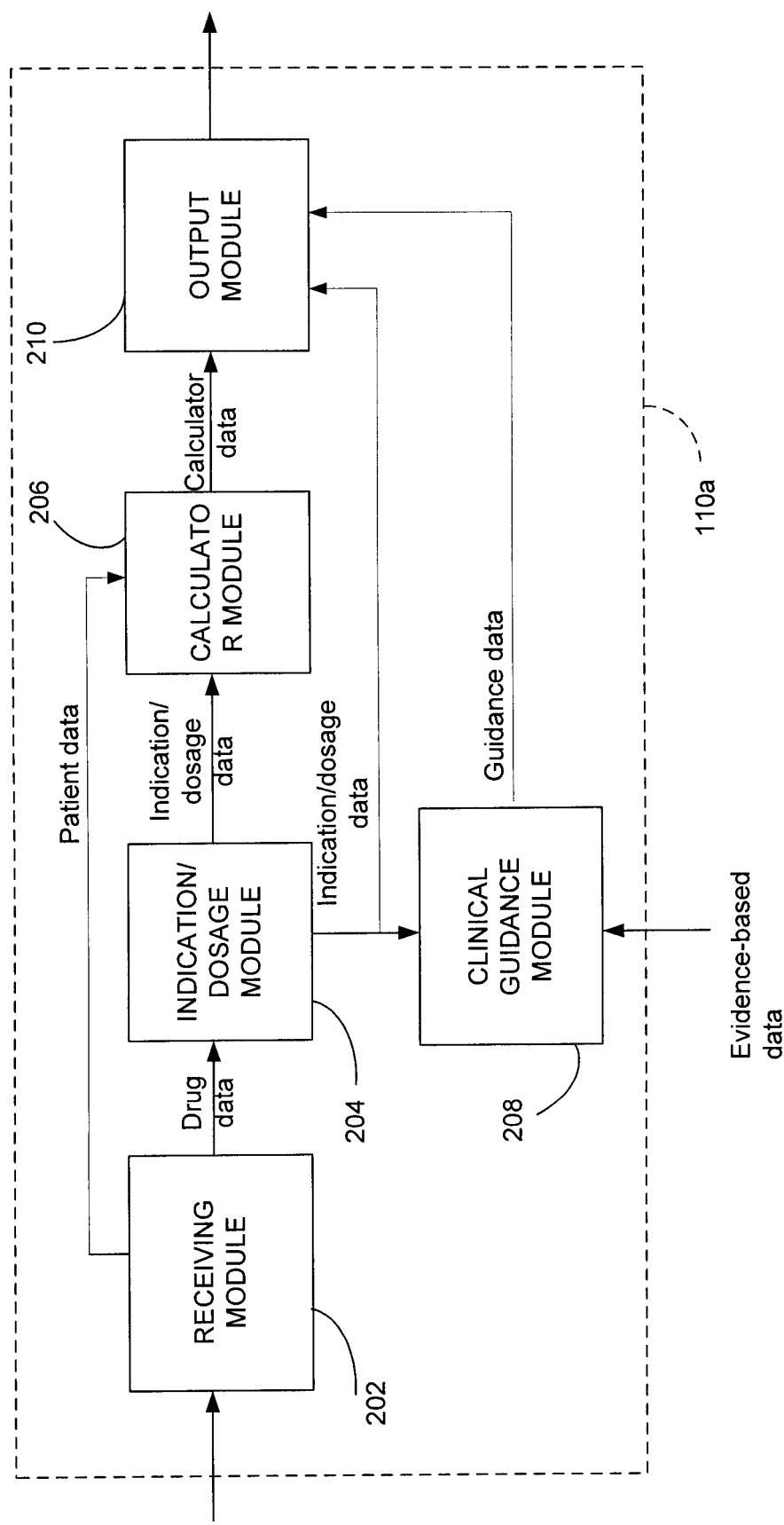
FIG. 2a is a block diagram showing an exemplary application running on the processor of FIG. 1.

FIG. 2a is an exemplary embodiment of an application 110a running on the processor 112. The application 110a may comprise a receiving module 202, an indication/dosage module 204, a calculator module 206, a clinical guidance module 208, and an output module 210.

The receiving module 202 may receive input data upon a user providing information to the drug formulary system 104 using his/her device 102. As will be discussed further below, after accessing the system 104, the user may enter the input data using a suitable interface presented on the device 102. Access to the drug formulary system 104 may be effected by launching an application downloaded on the device 102, as discussed above, or by accessing a website associated with the system 104. In the latter case, the user may be required to register with the system 104 and to log into the system 104 using a unique identifier, e.g. username and password, the user would have been provided with upon registering with the system 104.

The input data illustratively comprises drug data comprising a name of a drug for which the user wishes to obtain information. The received drug data may also comprise data indicative of a therapeutic class of the drug, e.g. antibiotic or anti-inflammatory. In another embodiment, the drug data may comprise an indication for which the drug is prescribed. It should be understood that in the latter case, the indication/dosage module 204 discussed in further detail below does not output indication information for the drug as this would already be known. The input data may further comprise patient data, which is specific to the patient, e.g. a small animal such as a dog or cat, to be treated. For example, the patient data may be indicative of a body weight of the animal. It should be understood that any other relevant input data may be supplied to the system 104 as needed.

The receiving module 202 may then send the drug data to the indication/dosage module 204, which determines and outputs from the received data the indication(s) the drug is suitable for (if not already provided to the system 104 as an input) and the appropriate drug dosage(s) for each indication. For this purpose, using the drug data as input, the indication/dosage module 204 queries the memory 114 and/or databases 116, which have stored therein drug product information or attributes. For instance, the memory 114 and/or databases 116 may store information including, but not limited to, the name, generic name, brand name(s), regional availability, indication(s), therapeutic class, contraindicated protocol(s), dosage(s), rate and mode of administration, animal species that can be treated, reference material, and the like, for each one of a plurality of drug products. The memory 114 and/or databases 116 may also store additional relevant information, as will be discussed further below.

The indication/dosage module 204 retrieves from the memory 114 and/or databases 116 all known uses or indications for which the drug indicated in the drug data may be prescribed. For each indication, the indication/dosage module 204 further retrieves the dosage(s) at which the drug may be prescribed as well as the animal species the drug may be indicated for. In one embodiment, the drug dosage may be output as a unit dose value and a total dosage may further be computed using any suitable calculator, as will be discussed further below. For each identified dosage, the indication/dosage module 204 may also retrieve the type of condition, e.g. acute, chronic, critical/refractory acute, the drug dosage is suited for along with details surrounding administration (e.g. intravenous, orally, as needed, continuous rate infusion, etc.) of the drug. Any idiosyncrasies or other particularities about the administration procedure may also be obtained. The indication/dosage module 204 may further retrieve additional information relevant to the drug, such as expected effects from administration thereof and commonly used combination treatments, e.g. other drugs, diets, protocols, and the like, that may be suitable for a given indication in combination while administering the drug at the suggested dosage (or treatment protocol). Also, the drug product information may be searchable by commercially available brand names, generic names, and regional availability, resulting in the indication/dosage module 204 outputting context aware treatment protocol (e.g. indication/dosage) suggestions for any given case. In particular, in determining the drug dosage suitable for the case at hand, the indication/dosage module 204 may make abstraction of the specific drug name and output information about the corresponding generic or regional brand, where applicable.

The indication/dosage module 204 then generates from the information retrieved from the memory 114 and/or databases 116 indication/dosage data that is sent to the clinical guidance module 208 for generating clinical guidance information, as will be discussed further below. The indication/dosage data is also sent to the calculator module 206, which may further receive from the receiving module 202 the patient data. The calculator module 206 then processes the received data and outputs calculator data indicative of the result(s) of calculation(s) performed by the calculator module 206, as will be discussed further below. In one embodiment, the calculator module 206 automatically accesses the indication/dosage data (e.g. indication, dosage, administration route, species the drug dosage is indicated for) without the user being prompted to provide such information. Also, in one embodiment, the calculator module 206 automatically determines calculations to be performed on the data, as will be discussed below, without the user being required to select a calculator to be used.

The indication/dosage data output by the indication/dosage module 204, the guidance data output by the clinical guidance module 208, and/or the calculator data by the calculator module 206 are then sent to the output module 210 for subsequent transmission to the devices 102. The output module 210 may then format the received data for rendering on an interface (not shown) presented on the devices 102. In another embodiment, the output module 210 may format the received data for transmission to the devices 102 via email, Short Message Service (SMS), Multimedia Messaging Service (MMS), instant messaging (IM), or other suitable communication means known to those skilled in the art.

Figure 2B:
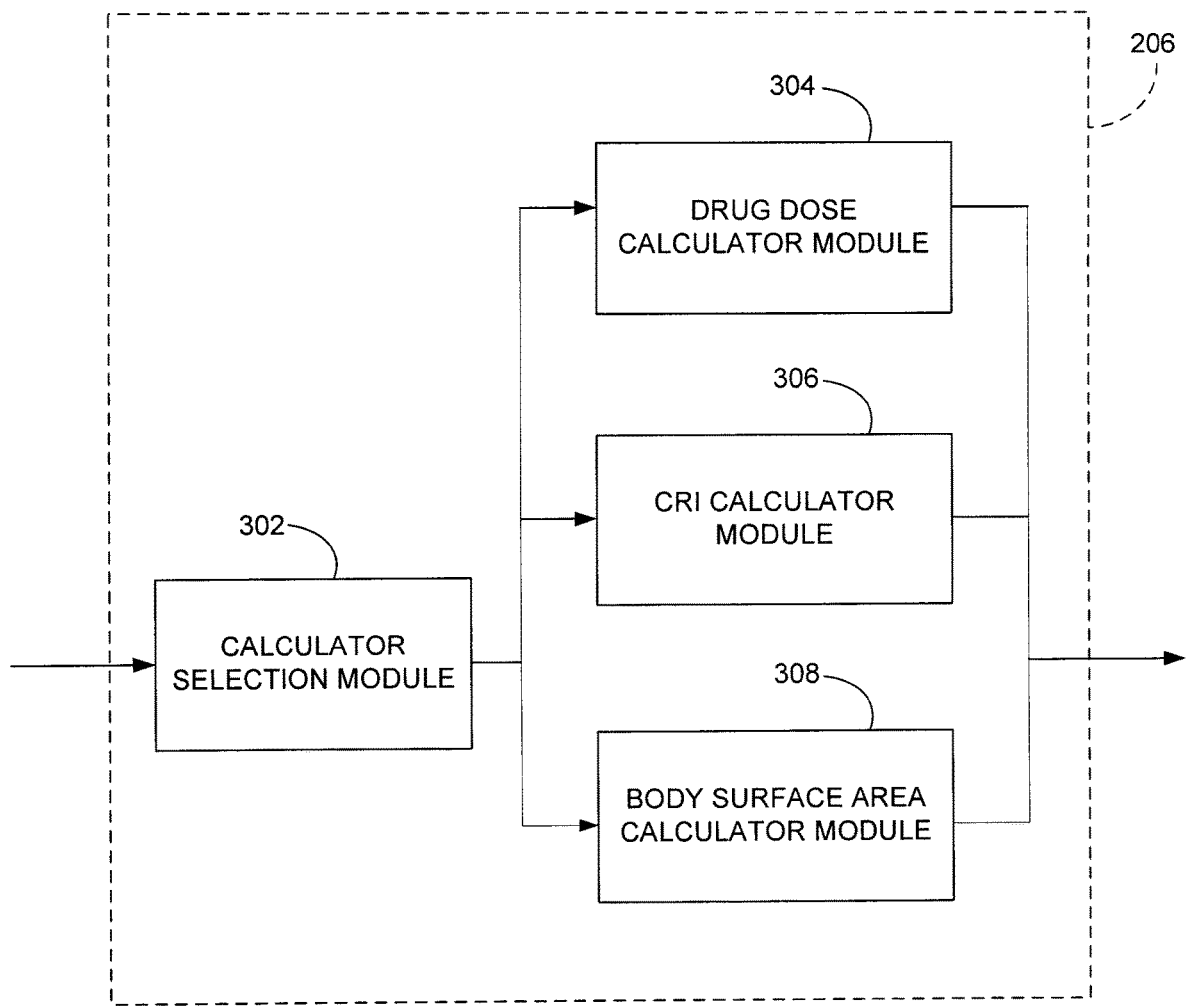

Referring now to FIG. 2b, the calculator module 206 illustratively comprises a calculator selection module 302, a drug dose calculator module 304, a Continuous Rate Infusion (CRI) calculator module 306, and a body surface area calculator module 308. It should be understood that, depending on the applications and on calculations to be performed by the calculator module 206, other modules may apply. For example, an emergency drug calculator module (not shown) may provide a dosage of emergency drugs for small animals to manage severe veterinary emergencies.

The calculator selection module 302 illustratively receives the indication/dosage data output by the indication/dosage module 204 along with the patient data from the receiving module 202 and determines the type of calculation(s) that are applicable to the case at hand. Indeed, depending on the drug as well as on the patient-specific information for the case at hand, different calculations may be performed. For instance, if the indication/dosage data indicates that the current drug is an analgesic agent (e.g. Ketamine or Lidocaine) to be administered via CRI, the calculator selection module 302 determines that CRI calculations apply for the case at hand. The calculator selection module 302 will then send the indication/dosage data and the patient data to the CRI calculator module 306. If the indication/dosage data indicates that the current drug is not a drug administered via CRI, then the calculator selection module 302 will determine that the CRI calculator module 306 is not to be used and the indication/dosage data and patient data will not be provided thereto.

In order to determine the computation(s) applicable to the case at hand, the calculator selection module 302 may query the memory 114 and/or databases 116 using the indication/dosage data and the patient data as input. The drug information stored in the memory 114 and/or databases 116 may indeed comprise calculation data indicative of calculation(s) relevant for each drug, indication, and dosage combination. In particular, the calculation data may indicate the calculations applicable (e.g. in accordance with the drug attributes stored in memory) for computing the total dosage of each drug. The memory 114 and/or databases 116 may also identify the drugs to be administered by continuous rate infusion and for which CRI calculations therefore apply.

Upon determining the suitable(s) calculator(s) to be used, the calculator selection module 302 then sends the patient data and the indication/dosage data to at least one of the drug dose calculator module 304, the CRI calculator module 306, and the body surface area calculator module 308 so that only the applicable calculations determined by the calculator selection module 302 are performed. The calculators 304, 306, 308 then each process the received data and output results of the calculations performed. For this purpose, formulas known to those skilled in the art may be used. In particular, the drug dose calculator module 304 calculates how much of the drug should be given to treat a given condition based on the patient's weight. This may be obtained by multiplying the weight with the unit dose value of the drug recommended for the given condition.

The CRI calculator module 306 illustratively computes CRI dosages to determine how much of the drug should be added to a specific volume of intravenous fluid to achieve a required dosage. In particular, the CRI calculator module 306 may obtain a recommended CRI dosage for the drug and compute a total volume of the drug to be added to a fluid container (e.g. an intravenous bag) used when administering the drug. The CRI calculator module 306 may also compute a drip or fluid rate for the fluid container. These computations may be performed using the recommended CRI dosage as well as the patient's weight, the concentration of the drug, the volume of the fluid container, and/or a duration of administration of the drug, as may be obtained from the received patient data.

The body surface area calculator module 308 illustratively computes the body surface area of the animal being treated for the purpose of determining the animal's drug dosages. For this purpose, the body surface area calculator module 308 may compute the body surface area of the animal using the animal's weight and height, as obtained from the received patient data. The total dosage of the drug may then be obtained from the computed body surface area and unit dose value of the drug for the given indication to be treated.

Figure 2C:
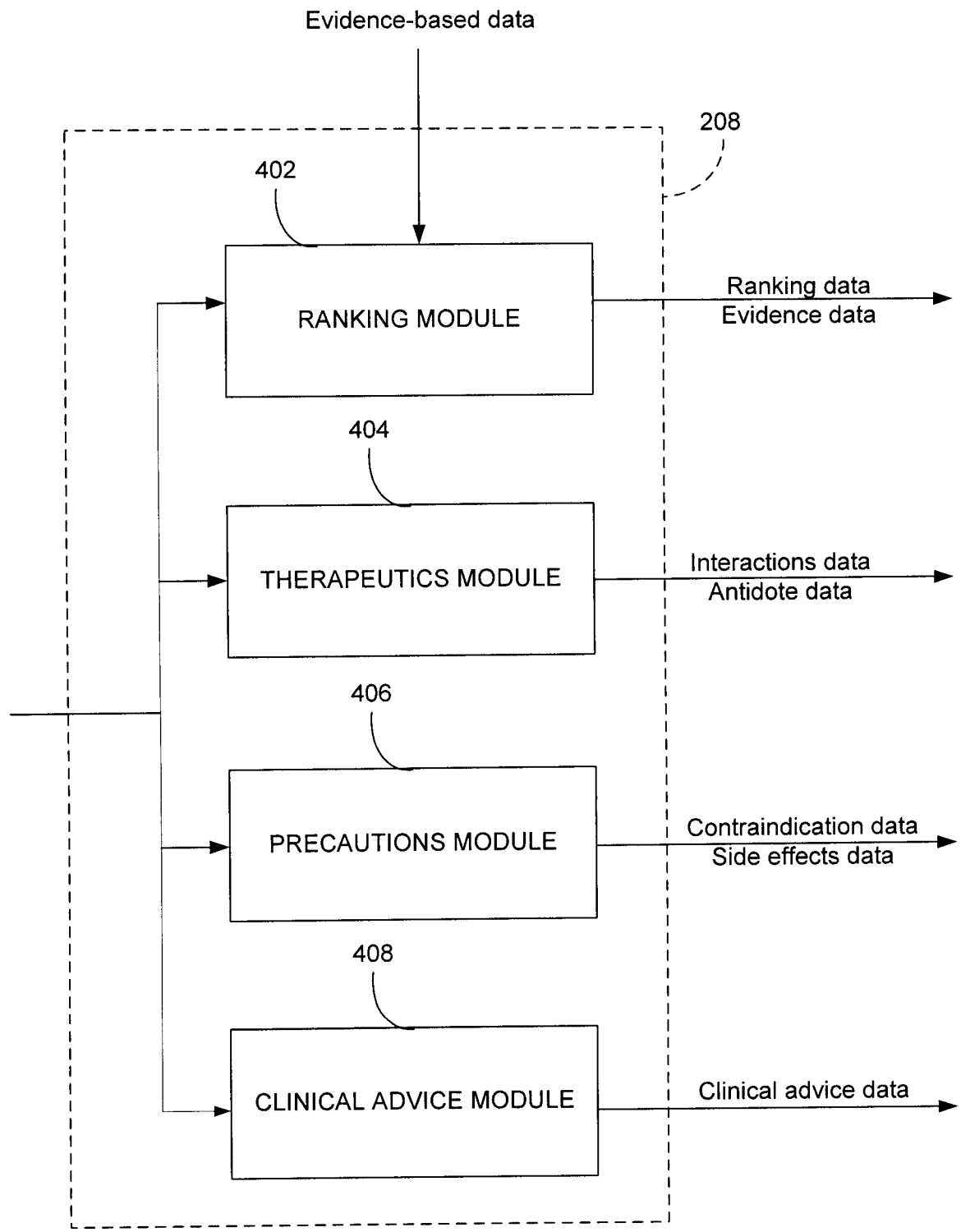

Referring now to FIG. 2c, the clinical guidance module 208 illustratively comprises a ranking module 402, a therapeutics module 404, a precautions module 406, and a clinical advice module 408. It should be understood that at least one of the modules 402, 404, 406, and 408 may be used and that other modules may apply if it is desired to provide other guidance information to the user.

The ranking module 402 is illustratively used for ranking the strength of evidence supporting a drug indication/dosage output by the indication/dosage module 204. In this manner, it becomes possible to rank the treatment efficacy of a suggested drug dosage (or treatment protocol). For this purpose, the ranking module 402 receives the indication/dosage data from the indication/dosage module 204 and retrieves from the memory 114 and/or databases 116 evidence-based data supporting the indication/dosage. The evidence-based data stored in the memory 114 and/or databases 116 may have been obtained from any suitable source, such as a clinical data warehouse or medical publication database. The evidence-based data may comprise case studies, clinical reports, clinical trial data, expert opinions, research papers, scholarly articles, magazine or periodical articles, peer-reviewed citations, and other relevant reference material. The evidence-based data may be indicative of a clinical effectiveness of one or more of the various drugs for which drug information is stored in the memory 114 and/or databases 116.

For each indication/dosage received from the indication/dosage module 204, the ranking module 402 retrieves from the memory 114 and/or databases 116 the evidence-based data associated with the indication/dosage. The ranking module 402 may then determine how strong the evidence is for the indication/dosage in question. For this purpose, the ranking module 402 may be configured to define a scale having several ranking levels, each level being indicative of a level of strength for the evidence. For instance, the multi-level scale may comprise five (5) levels, with level five (5) being attributed to the most convincing evidence and level one (1) being attributed to the least convincing evidence. It should be understood that other ranking levels may apply. In one embodiment, the ranking levels may be defined in accordance with the type of evidence the scale is based on. For instance, level one (1) may be associated with meager evidence, such as a one case/pharmacokinetic study without clinical efficacy. Level two (2) may be associated with supportive evidence, such as a retrospective study without control subjects. Level three (3) may be associated with substantive evidence, such as a prospective study without blinding, randomization, or controls. Level four (4) may be associated with robust evidence, such as a prospective study with some randomization, blinding, or controls. Level five (5) may be associated with conclusive evidence, such as a prospective study that is controlled, randomized, and blinded.

It should be understood that the ranking levels may be defined on the basis of any type of evidence or study (e.g. prospective vs. retrospective). It should also be understood that other determining factors or attributes, which may consistently and accurately portray the relevance of the evidence, may be used to define the ranking levels. For instance, in addition to the type of evidence and/or study, the ranking levels may be defined on the basis of factors including, but not limited to, the type of blinding (e.g. non-blinded, single-blinded, double-blinded, triple-blinded/masked), the type of control (e.g. none, placebo control, negative control, positive/comparison control), randomization, sample/control group size, number of trials, assessment of whether an animal signalment is provided, and assessment of whether the indicated and target species are the same. Each ranking level may then be associated with a combination of attributes.

It should also be understood that, in some embodiments, the ranking module 402 may not define the ranking levels in the manner discussed above. Indeed, the ranking levels may be determined by assignment by medical expert(s) or other suitable person rather than generated by the ranking module 402. In this case, the ranking levels may be sent by the person in question to the system 104 and received at the receiving module 202. The receiving module 202 may then transmit the received ranking levels to the clinical guidance module 208 for use by the ranking module 402 to output a measure (e.g. a visual scale) indicative of the confidence level in the evidence, as discussed further below.

By correlating the retrieved evidence to the defined ranking levels, the ranking module 402 may attribute a rank to the evidence supporting the suggested indication/dosage and output the ranking. The ranking module 402 may also output the retrieved evidence that supports the suggested indication/dosage and from which the ranking has been determined. The data output by the ranking module 402 may then be sent to the output module (reference 210 of FIG. 2a) for rendering on the devices (reference 102 of FIG. 1). The ranking data may be formatted so as to be presented to the user as a visual scale but it should be understood that other scales may be used. In one embodiment, the visual scale may be a bar scale comprising several bars, with each bar being associated with a given ranking level. The visual scale may then indicate the ranking of the suggested indication/dosage relative to the available rankings, e.g. a ranking of four (4) out of five (5). Using such a visual scale, the user can then weight the strength of the evidence supporting the suggested indication/dosage and assess the level of confidence in the indication/dosage. In particular, the user can visually identify the treatment of choice, namely the treatment supported by the strongest evidence, i.e. with the highest level on the visual scale. On the basis of the available evidence, it can then be ensured that the most effective drug is suggested to the user. In addition, the evidence data supporting the indication/dosage may be presented for reference to the user who is then provided with tools allowing him/her to make an informed decision.

It should be understood that a given drug dosage that is selected as the treatment of choice at one point in time may no longer be the treatment of choice at a later point in time. Indeed, new evidence may emerge, resulting in the ranking module 402 revising the ranking level assigned to the evidence supporting the current treatment of choice. The new evidence may also result in the ranking module 402 attributing a higher ranking level to evidence supporting another drug dosage, which then becomes the new treatment of choice. A current treatment of choice may therefore be surpassed by another treatment at any point in time. The processing performed by the ranking module 402 may therefore be dynamic and updates may be generated periodically whenever changes to the ranking levels of a given drug dosage occur as a result of the evidence-based data being updated.

Although described herein as being used for assessing the strength of evidence used for drug formulary applications, it should be understood that the visual scale and associated ranking levels defined by the ranking module 402 may also apply to any treatment-based application using evidence-based medicine.

Still referring to FIG. 2c, the therapeutics module 404 illustratively receives the indication/dosage data from the indication/dosage module (reference 204 in FIG. 2a) and retrieves from the memory 114 and/or databases 116 therapeutic information related to the drug at hand. The retrieved therapeutic information may comprise information about interactions and/or information about antidotes and reversal agents for the given drug. Other therapeutic information may apply. The retrieved therapeutic information is then output by the therapeutics module 404 and sent to the output module (reference 210 of FIG. 2a) for rendering on the devices (reference 102 of FIG. 1).

The precautions module 406 further illustratively receives the indication/dosage data from the indication/dosage module 204 and retrieves from the memory 114 and/or databases 116 precaution information related to the drug at hand. The retrieved precaution information may comprise information about precautions to be taken when administering the drug. For instance, information about contraindications or adverse side effects of the drug may be obtained. The retrieved precaution information is then output by the precautions module 406 and sent to the output module 210 for rendering on the devices 102.

The clinical advice module 408 further illustratively receives the indication/dosage data from the indication/dosage module 204 and retrieves from the memory 114 and/or databases 116 clinical advice information for the drug at hand. The clinical advice stored in the memory 114 and/or databases 116 may come from recognized experts in the field and may comprise general tips and advice as to how to treat a given indication using the selected drug. The retrieved clinical advice information is then output by the clinical advice module 408 and sent to the output module 210 for rendering on the devices 102.

Figure 3:
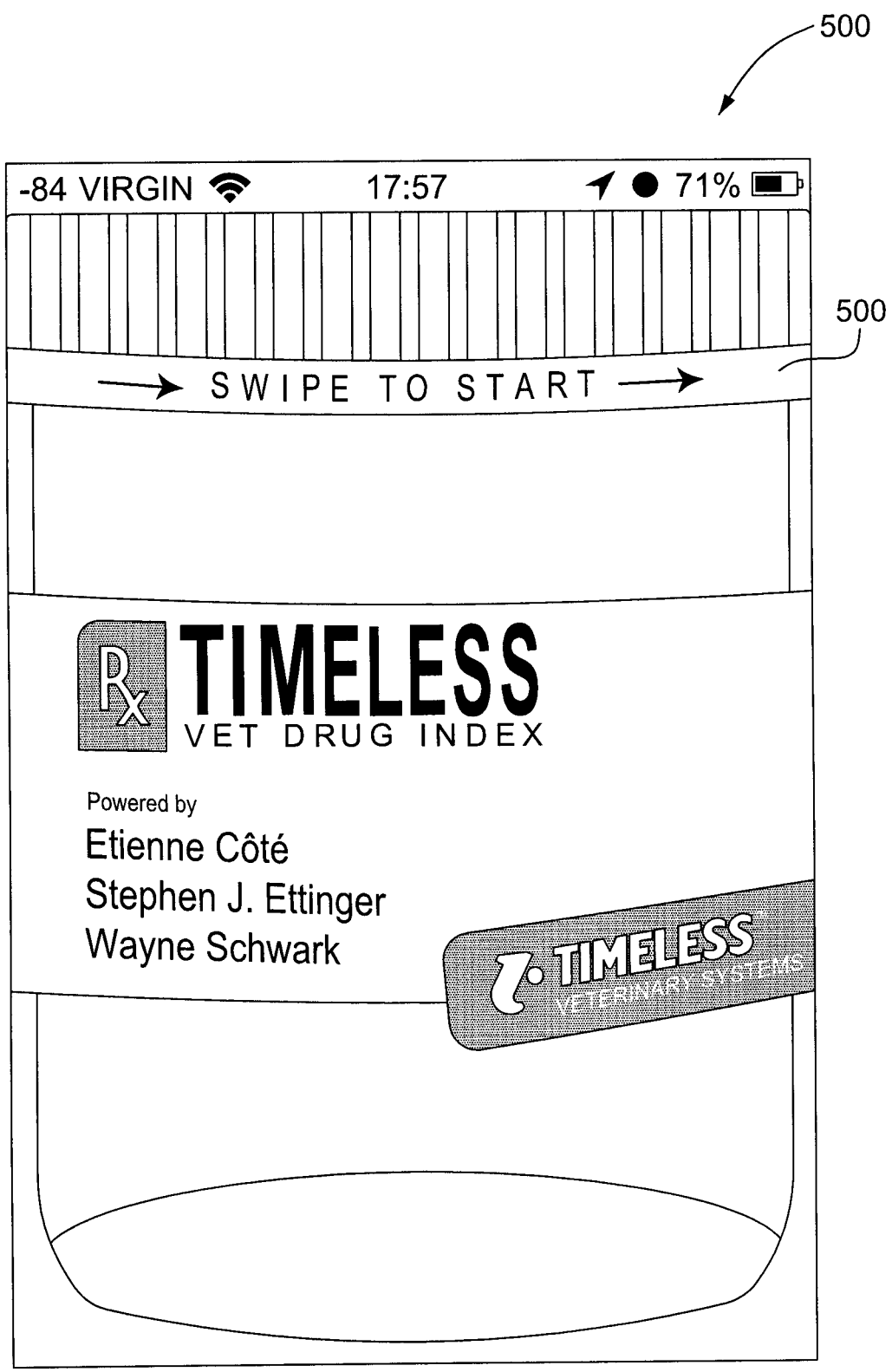
FIG. 3 is a screen capture of a main interface, in accordance with an illustrative embodiment of the present invention.

FIG. 3 illustrates a screen capture of a main interface 500 presented on a device 102 accessing the drug formulary system 104. The interface 500 comprises an option 502 that may be selected by the user to access the various features provided by the drug formulary system 104. In one embodiment, the option 502 is a "Swipe to start" option that provides access to the system 104 upon the user effecting a right swipe on the option 502. It should however be understood that the option 502, as well as any other option discussed herein, may be any suitable control element that may be selected by a user using any action or gesture known to those skilled in the art (e.g. click, tap, pinch, drag, scroll, left swipe, etc.). The options discussed herein may be selected using any suitable input device (not shown), such as a touchscreen, a mouse, or the like, provided with the device 102.

Figure 4:
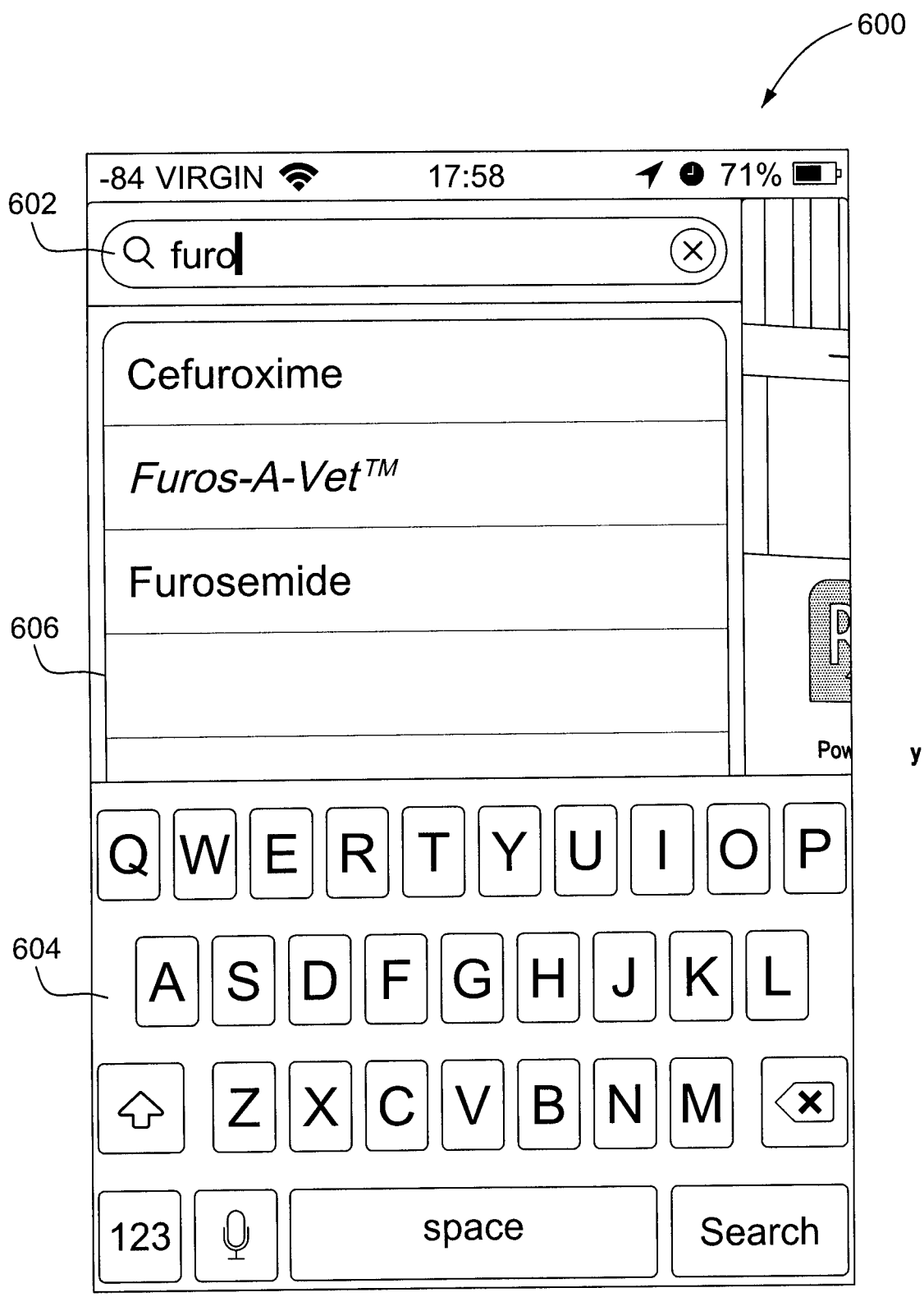
FIG. 4 is a screen capture of a drug list and search screen, in accordance with an illustrative embodiment of the present invention.

Referring to FIG. 4, upon the user selecting the option 502, a drug list and search screen 600 is presented to the user. The screen 600 illustratively comprises a search bar 602 enabling the user to enter search terms, e.g. enter a drug name to be searched, using a suitable input means, such as a virtual keypad 604 presented on the screen 600. Other input means (not shown) may apply. Upon the user entering the search terms in the search bar 602, a subset of drug names matching the entered search terms may be listed in a box 606. In one embodiment, the user need not enter the full drug name in the search bar 602 but may only enter the first few letters of the drug name in order for matches to be listed in the box 606. The user may then select a given drug name from the list in box 606 to access the corresponding drug information. Once the user has selected the name of the drug for which information is desired, a drug screen 700 may be presented to the user, as shown in FIG. 5.

Figure 5:
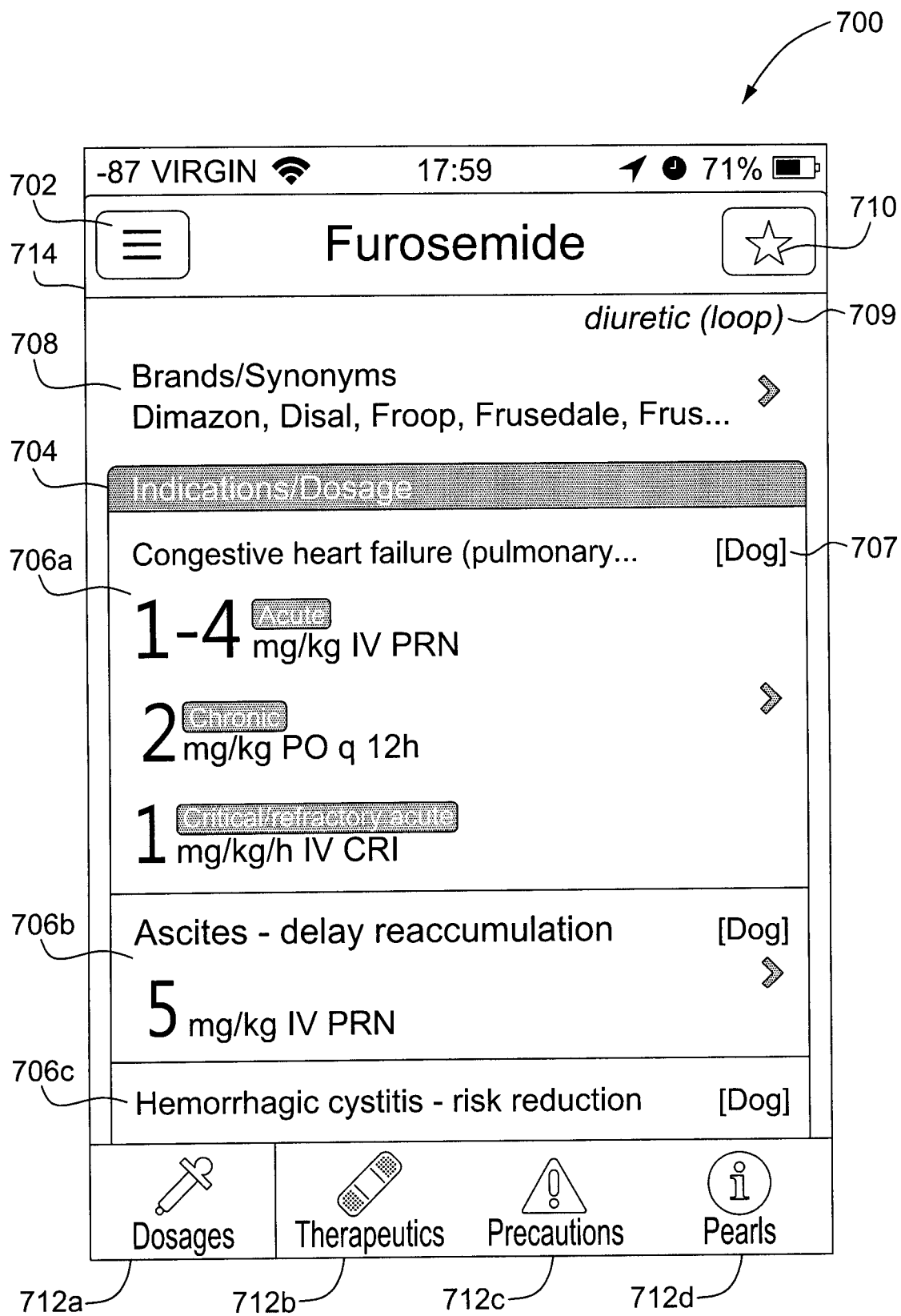
FIG. 5 is a screen capture of a drug screen, in accordance with an illustrative embodiment of the present invention.
Figure 6:
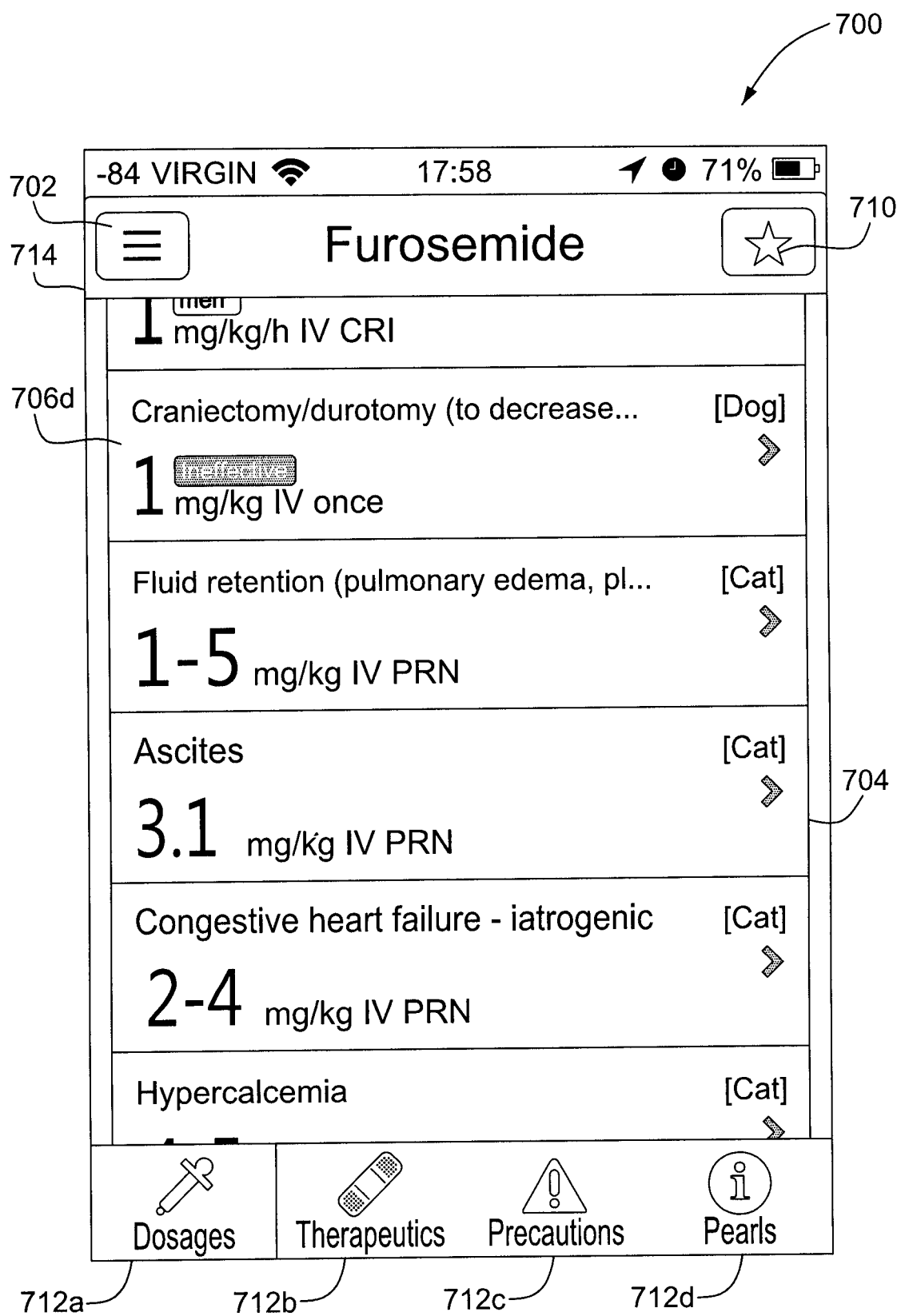
FIG. 6 is a screen capture of a drug screen showing a contraindicated protocol, in accordance with an illustrative embodiment of the present invention.

The drug screen 700 of FIG. 5 illustratively comprises a header box 702, in which the name of the selected drug, e.g. Furosemide, is indicated. The screen 700 illustratively comprises an "Indications/Dosage" section 704 listing indication(s) and dosage information (e.g. unit dose value) related to the drug at hand. Each indication is presented in a corresponding area 706a, 706b, 706c of the section 704 along with one or more dosages associated therewith. The animal species 707 (e.g. dog in the example of FIG. 5) the drug is suitable for treating for a given indication may also be provided. Each dosage may be associated with an option (not shown), which, upon being selected, provides the user additional information about the selected indication and dosage combination, as will be discussed further below. As shown in FIG. 6, contraindicated protocols may be presented in an area 706d of the Indications/Dosage section 704 along with indicated protocols. In one embodiment, the contraindicated protocols are displayed so as to be visually distinguishable from the indicated protocols presented in section 704. For example, the contraindicated protocols may be displayed in one colour while indicated protocols are displayed in another colour. It should be understood that other means of distinguishing contraindicated protocols from indicated protocols may apply.

Figure 7:
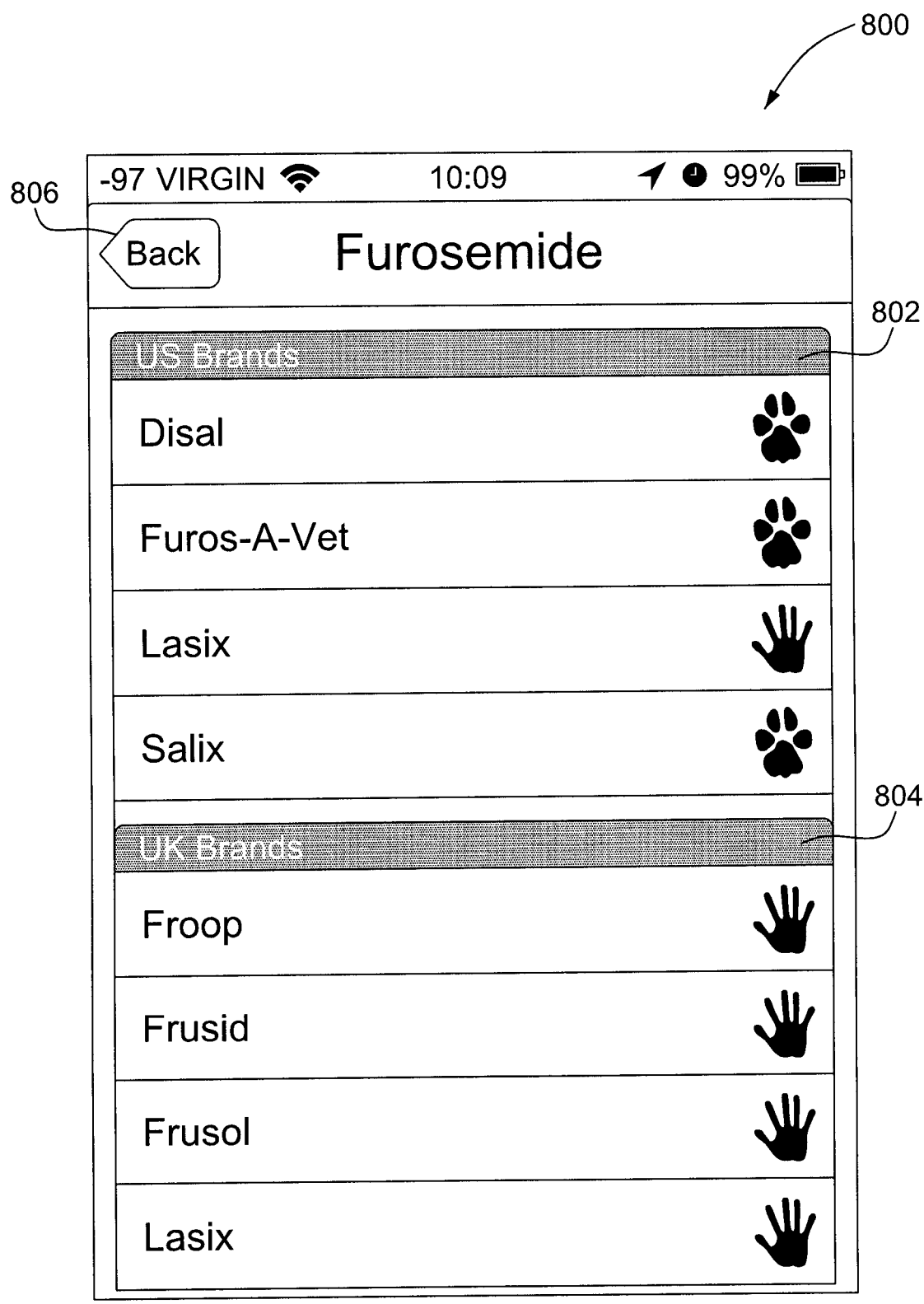
FIG. 7 is a screen capture of a brand/synonyms screen, in accordance with an illustrative embodiment of the present invention.

Referring back to FIG. 5, the drug screen 700 further comprises a "Brand/Synonyms" section 708, in which synonyms and/or generic brand names corresponding to the searched drug name are presented. The therapeutic class 709 (e.g. diuretic in the example of FIG. 5) may further be indicated. In one embodiment, the "Brand/Synonyms" section 708 is provided with a selectable option, which, upon being selected, directs the user to a "Brand/Synonyms" screen 800 shown in FIG. 7. The screen 800 illustratively lists regional brands associated with the drug in question. For instance, for the Furosemide drug, US brands are listed in a first section 802 of screen 800 while UK brands are listed in a second section 804 of the screen 800. It should be understood that other regional brands may also be listed. The screen 800 includes a "Back" option 806, which, upon being selected, enables the user to return to the drug screen 700 of FIG. 5.

Figure 8:
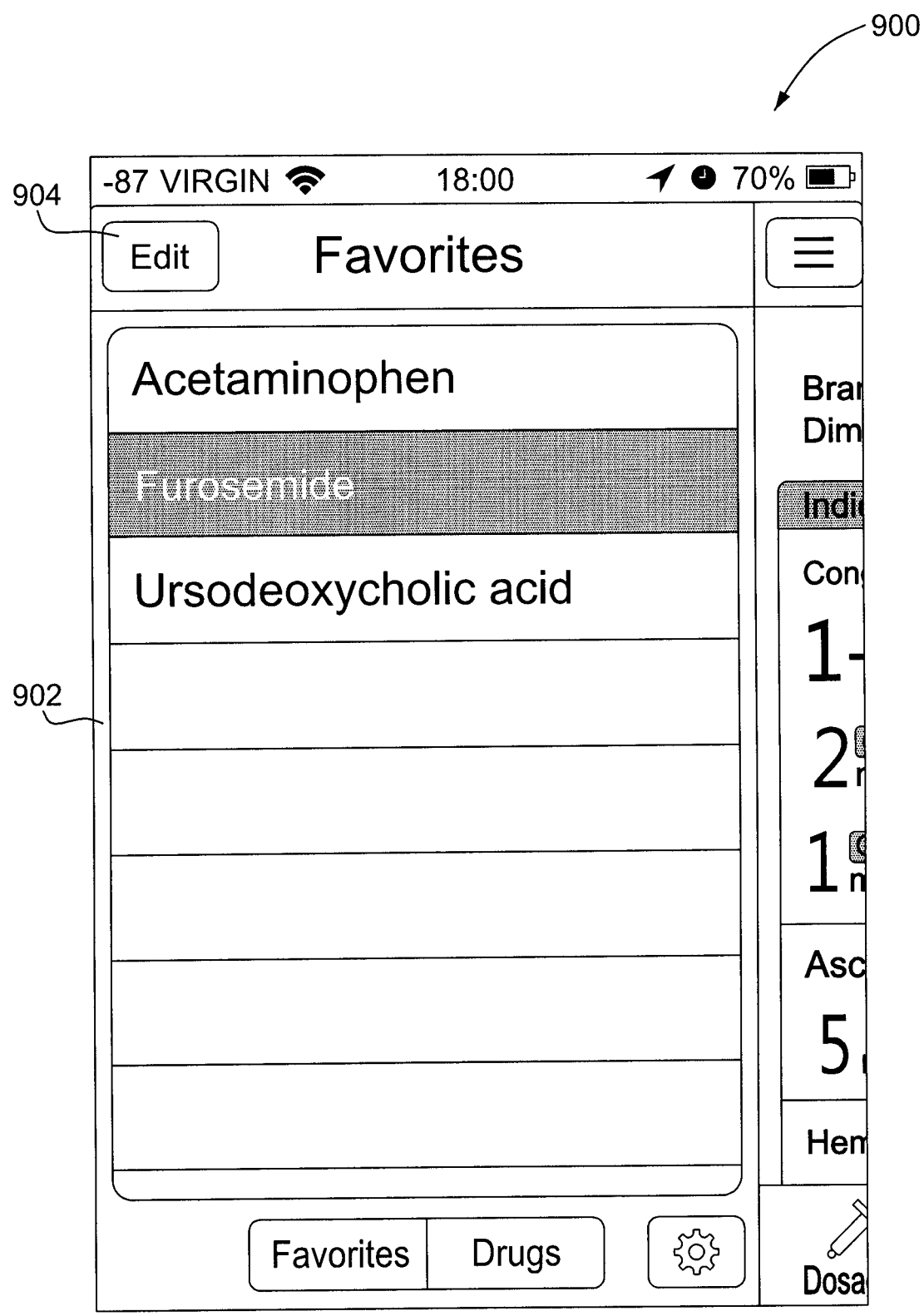
FIG. 8 is a screen capture of a favorites screen, in accordance with an illustrative embodiment of the present invention.

Referring now to FIG. 8 in addition to FIG. 5, the header box 702 further comprises a "Favorites" option 710 that, when selected enables the user to add the drug currently viewed, e.g. Furosemide, to the list of user's favorites, e.g. drugs of interest to the user that may be stored in a separate list for easy access. Upon selecting the "Favorites" option 710, the user is presented with a favorites screen 900 listing in a section 902 of the screen 900 drugs that are among the user's favorites. An "Edit" option 904 is further presented on the favorites screen 900 to allow the user to edit preferences associated with any drug listed in the section 902.

Still referring to FIG. 5, the screen 700 is illustratively a tab-based interface that comprises a plurality of icons 712a, 712b, 712c, 712d each associated with the information presented therein. For instance, the indication and dosage information shown in FIG. 5 is associated with the "Dosages" icon 712a. As will be discussed further below, the user may access therapeutics information by selecting the "Therapeutics" tab 712b, precautions information by selecting the "Precautions" tab 712c, and clinical advice information by selecting the "Pearls" icon 712d. It should be understood that other configurations may apply.

Figure 9:
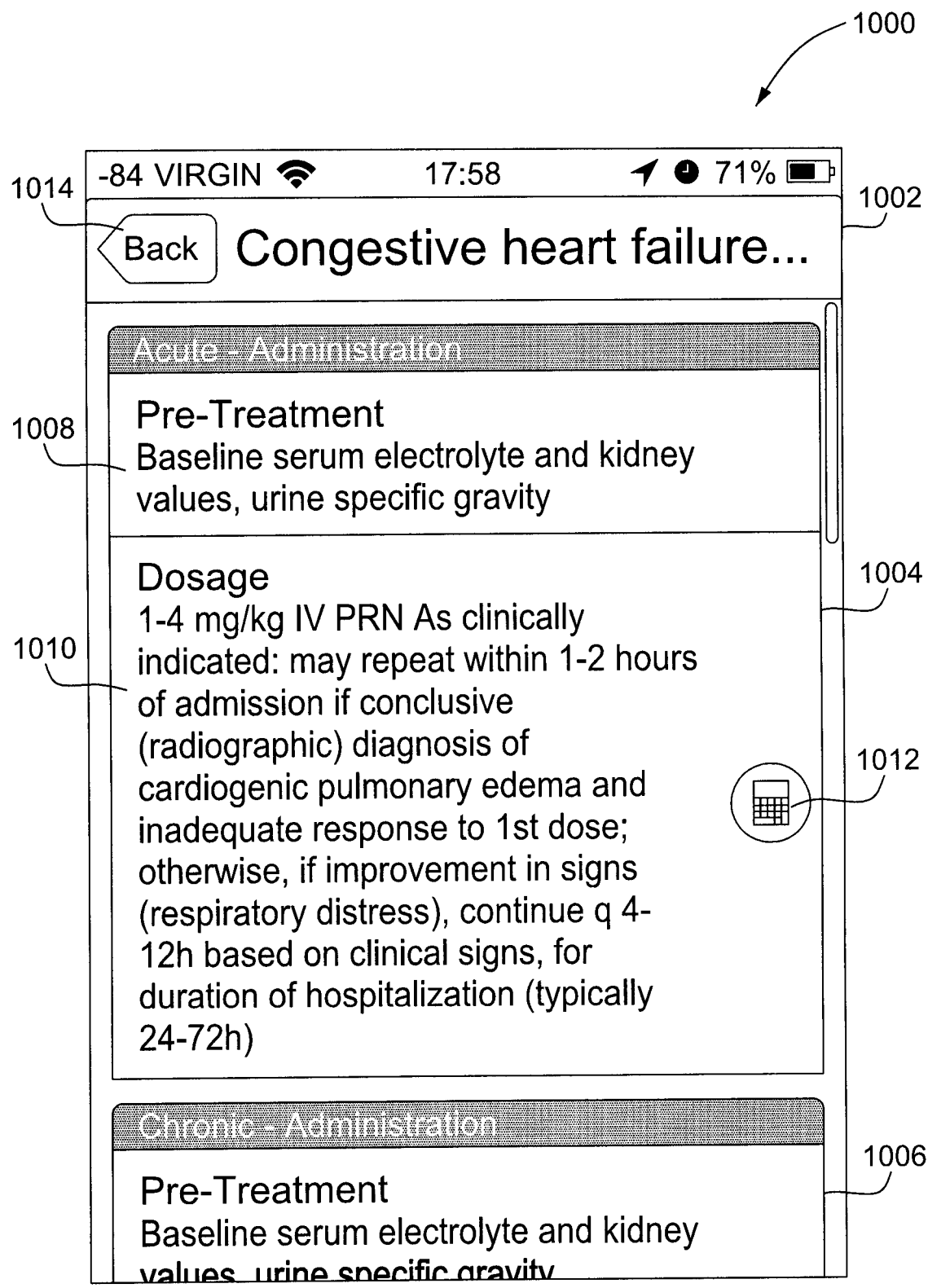
FIG. 9 is a screen capture of an indication screen, in accordance with an illustrative embodiment of the present invention.

Upon the user selecting an option corresponding to a given indication/dosage listed in an area 706a, 706b, 706c of the Indications/Dosage section 704 shown in FIG. 5, an indication screen 1000 is presented, as shown in FIG. 9. The indication screen 1000 comprises a header box 1002 providing an indication of the indication/dosage, e.g. congestive heart failure, for which information is presented. The indication screen 1000 further comprises a first "Acute—Administration" section 1004 providing information for treating acute conditions using the drug and a second "Chronic—Administration" section 1006 providing information for treating chronic conditions using the drug. It should be understood that additional information may also be provided. The section 1004 illustratively comprises a "Pre-treatment" area 1008 providing information about suitable pre-treatment for the patient prior to administering the drug and a "Dosage" area 1010 providing information about administration of the drug at the prescribed dosage. The "Dosage" area 1010 comprises an option 1012, which, upon being selected, directs the user to a dosage calculator tool. The user may return to the drug screen 700 of FIG. 5 upon selecting a return option 1014.

Figure 10A:
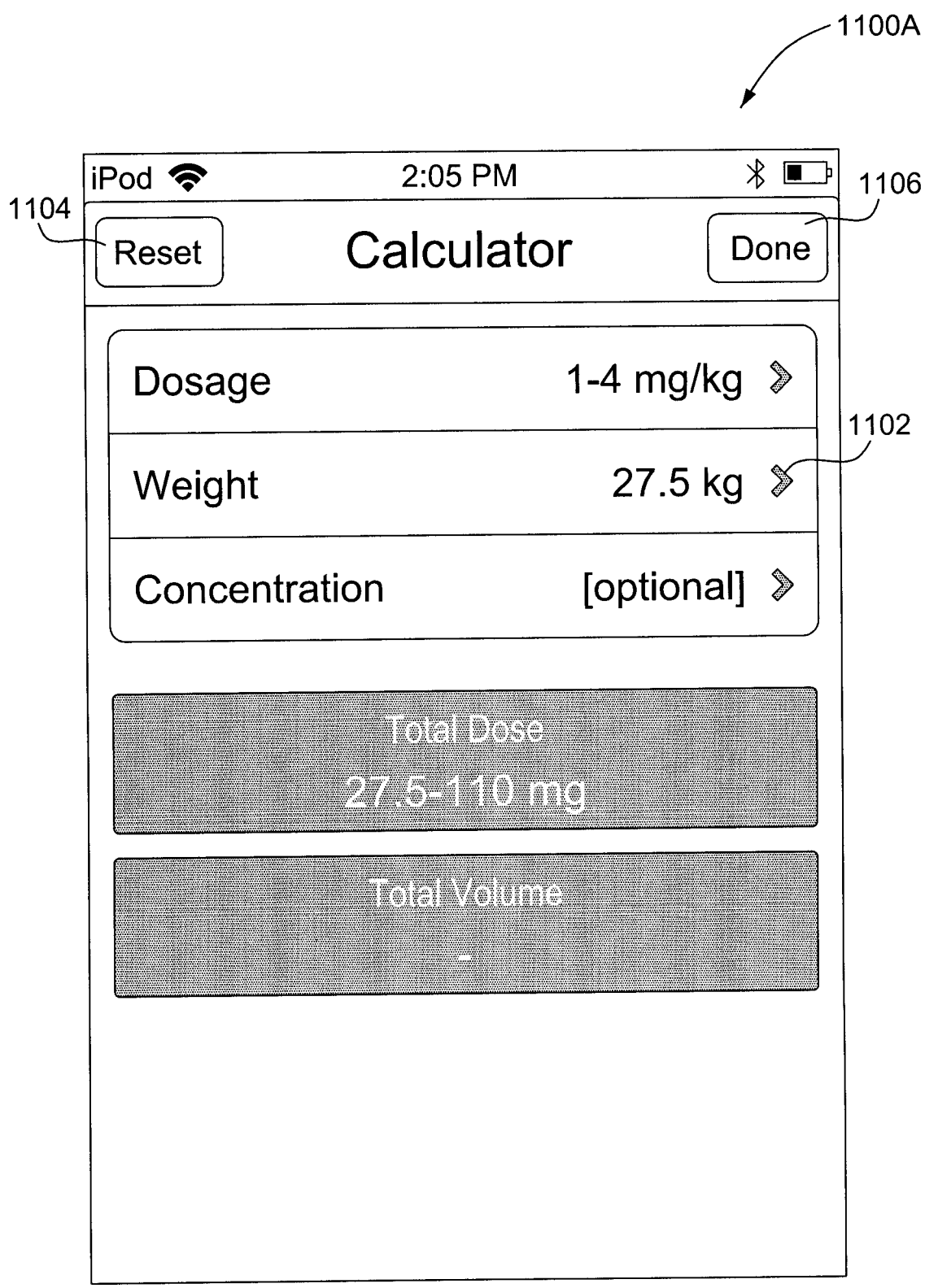
FIG. 10a is a screen capture of a dosage calculator screen, in accordance with an illustrative embodiment of the present invention.

As shown in FIG. 10*a*, upon the user selecting the option 1012 of FIG. 9, a dosage calculator screen 1100A is illustratively presented. The screen 1100A presents the user with information about the unit dose value indicated for the case at hand. One or more user interface elements, such as drop-down menus as in 1102 or text boxes (not shown) allowing for several lines of free text to be entered, may be provided to enable the user to submit patient data, such as body weight. It should be understood that other control elements may be used. The patient data may be entered using a suitable input means, such as a virtual keypad (not shown), that may be presented on the screen 1100A. Once the body weight has been entered, the dosage is calculated and output to the screen 1100A. In the illustrated example, the unit dose is 1-4 mg/kg for acute administration of Furosemide to treat congestive heart failure in a dog. Upon the user specifying that the animal's body weight is 27.5 kg (and optionally the concentration), the dose calculator processes the received data and outputs a calculated dose of 27.5-110 mg. Any data submitted to and/or output by the dosage calculator (or any other calculator discussed herein) may be reset by the user selecting a corresponding feature 1104.

Figure 10B:
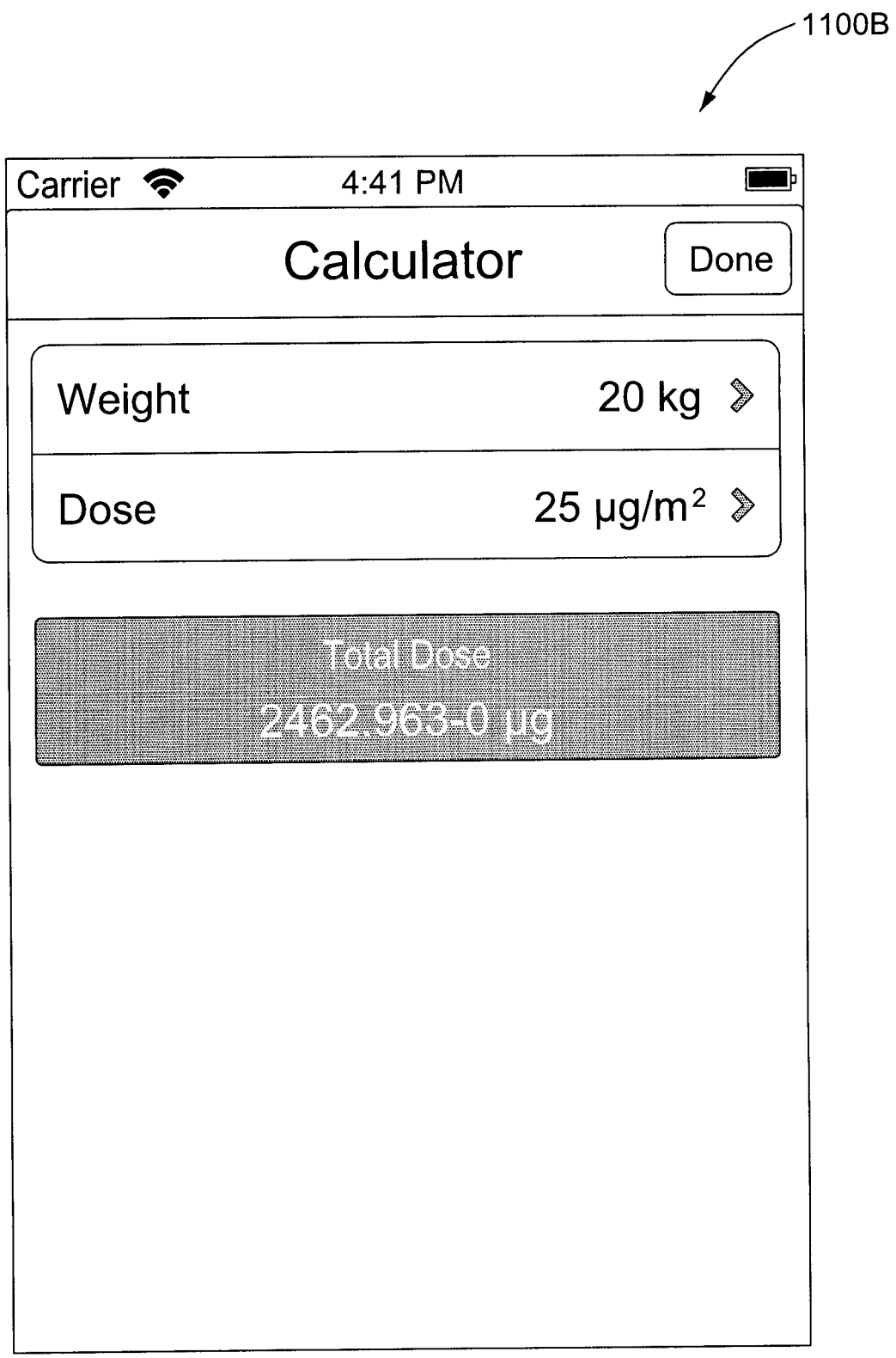
FIG. 10b is a screen capture of a body surface area calculator, in accordance with an illustrative embodiment of the present invention.
Figure 10C:
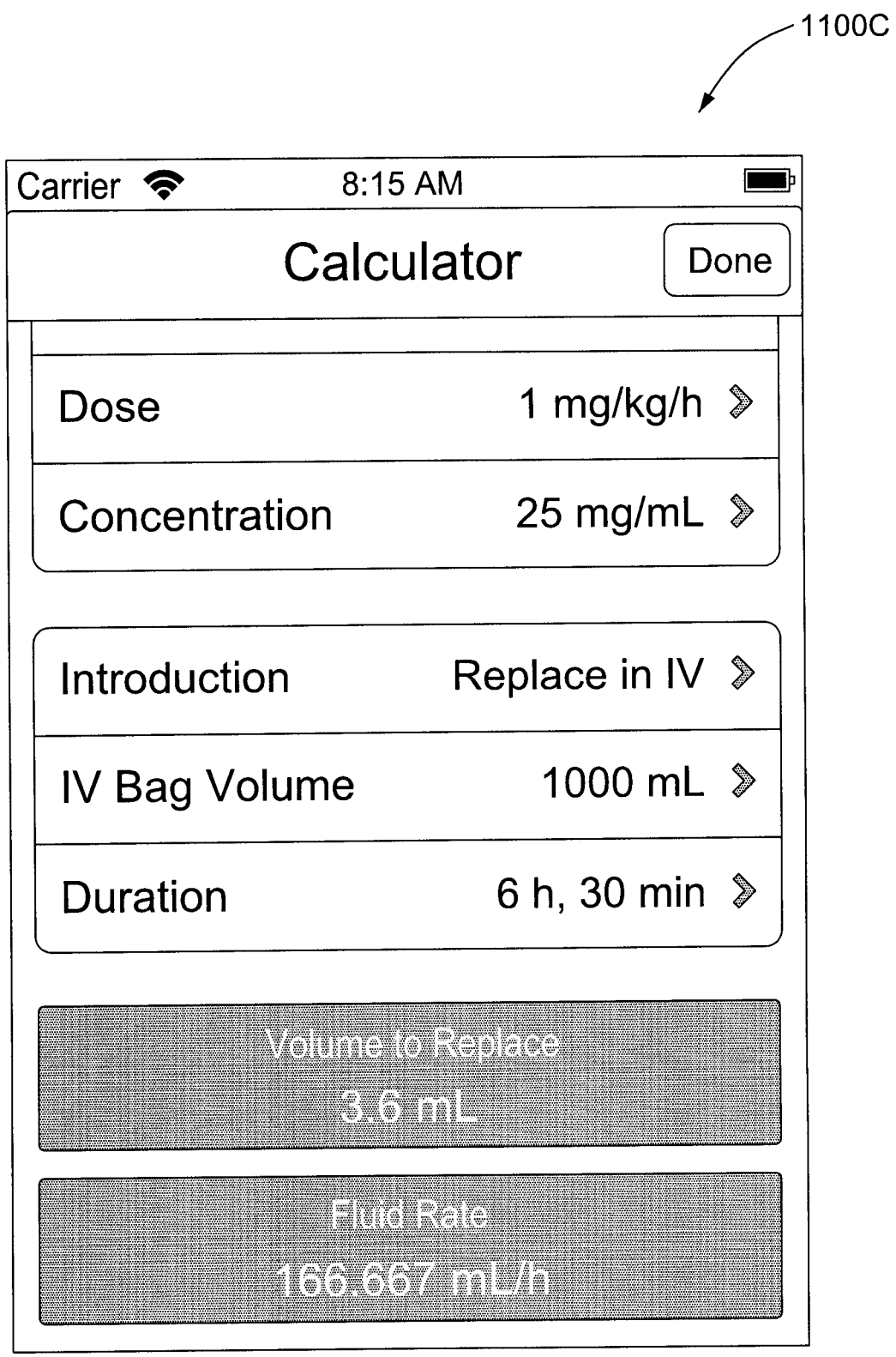
FIG. 10c is a screen capture of a CRI calculator, in accordance with an illustrative embodiment of the present invention.

Once the calculated dose has been output, the user may proceed with additional calculations if need be or return to the indication screen 1000 of FIG. 9 by selecting a corresponding option 1106. In one embodiment, the system may present the user with more calculators for performing additional calculations relevant to the case at hand. Indeed, as shown in FIG. 10*b* and FIG. 10*c*, it should be understood that calculators other than the dose calculator shown in FIG. 10*a* may be used. As discussed above, a body surface area calculator and/or a CRI calculator, respectively presenting the user with dosage calculator screens 1100B and 110C that enable entry of patient data and output a calculated dose (e.g. a total dosage of a given drug), may apply. For any of the calculators discussed herein, the indication/dosage data (e.g. the unit dose) and/or patient data (e.g. weight) or other input data received from the user may be pre-populated into the calculator without the user being prompted to enter (or resubmit) the data. Using this pre-populated data, the calculators automatically calculate a dose (e.g. in the case of the body surface area calculator, a total dose to be provided to the animal according to the computed body surface area or, in the case of the CRI calculator, the CRI dosage, e.g. the volume to be added to the fluid container and the drip rate of the fluid container, as discussed above), which is then output on the corresponding screen 1100A, 1100B, and/or 1100C. In addition, as discussed above, the system may automatically determine the calculator(s) to be used without requiring any input from the user.

Figure 11A:
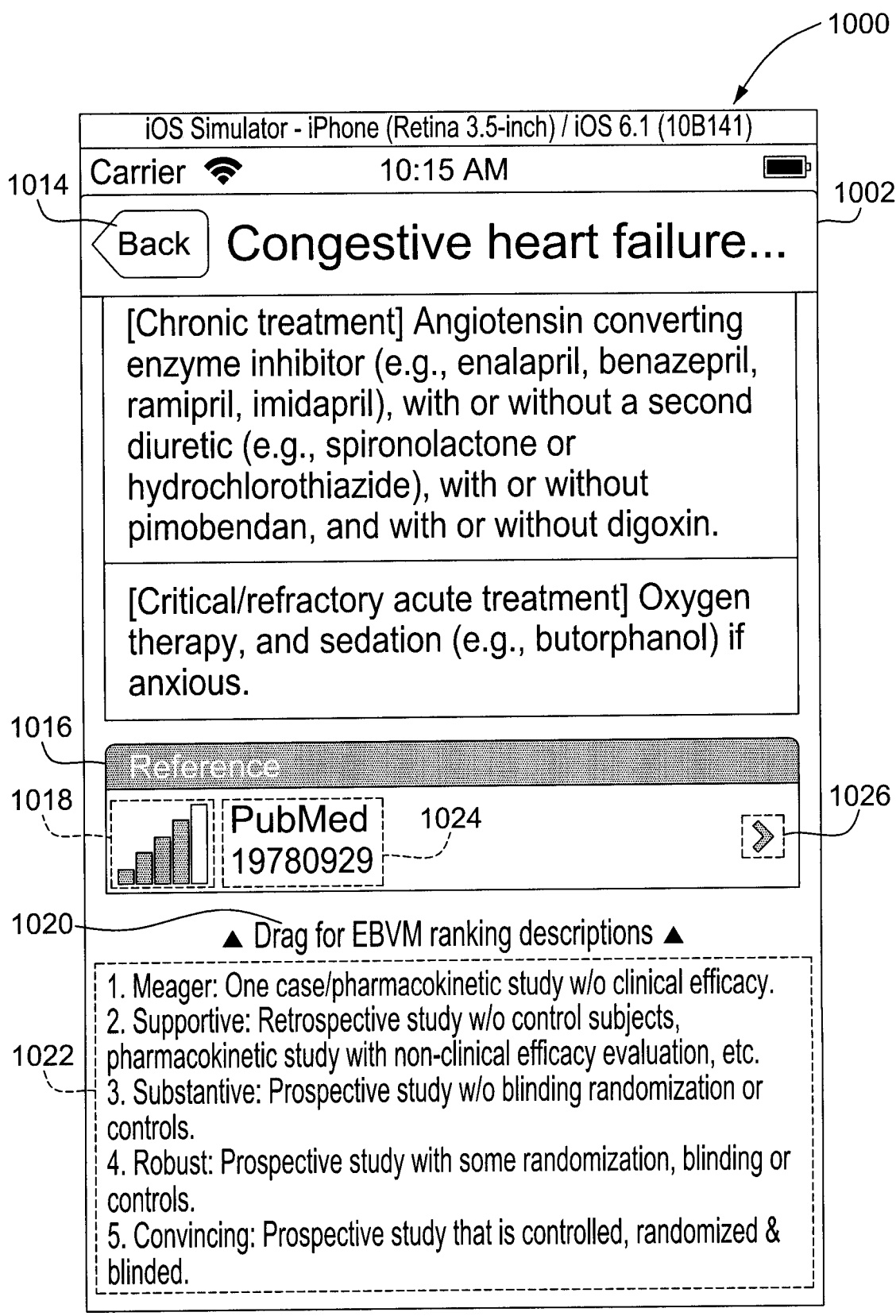
FIG. 11a is a screen capture of an indication screen showing a visual scale, in accordance with an illustrative embodiment of the present invention.

Referring to FIG. 11*a*, the indication screen 1000 may also comprise a reference section 1016. The reference section 1016 illustratively provides a visual scale 1018 that indicates the strength of the evidence supporting the suggested indication/dosage, as discussed above with reference to FIG. 2*c*. In the illustrated example, a rank level of four (4) out of a total of five (5) levels is associated with the reference supporting the suggested indication/dosage. It should be understood that, although a single piece of evidence is shown for illustrative purposes in reference section 1016 as supporting the indication/dosage, several references may support any given indication/dosage. In the latter case, several pieces of evidence may be displayed in the reference section 1016 and each provided with a corresponding visual scale 1018 indicating the strength of the piece of evidence. The user may then compare the strength of evidence supporting various indication/dosage suggestions in order to determine the best treatment for the case at hand, i.e. the treatment having evidence with the highest ranking level.

Figure 11B:
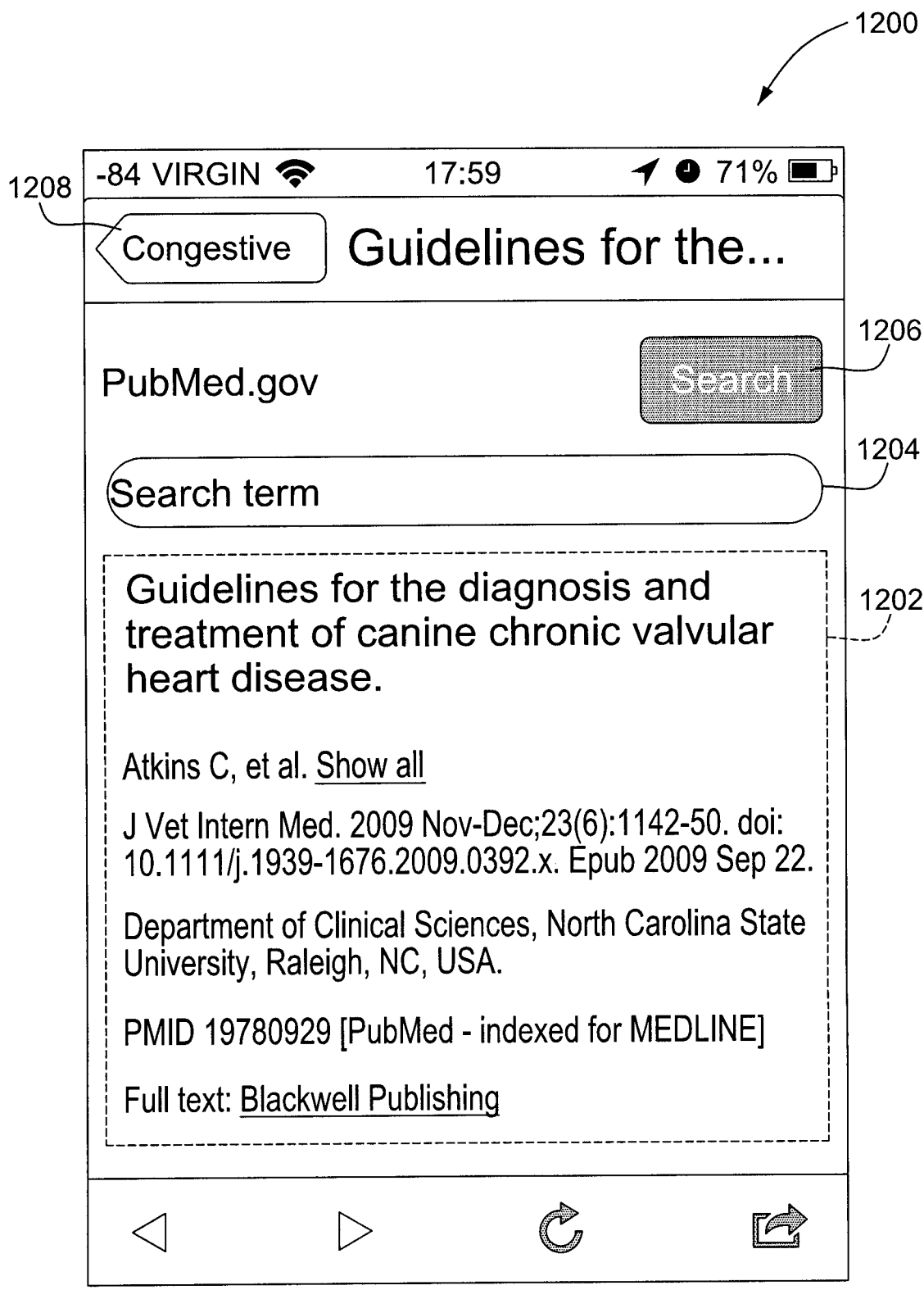
FIG. 11b is a screen capture of a reference screen, in accordance with an illustrative embodiment of the present invention.

Upon selecting an option 1020, the user may be provided with a description 1022 of the ranking levels used for the visual scale 1018. Details related to each piece of evidence may also be provided in a details area 1024 of the reference section 1016. Such details may comprise a unique identifier, e.g. a PubMed™ identifier (as illustrated), associated with the piece of evidence. The title of the source material may also be provided. Upon selecting an option 1026, the user may be directed to a reference screen 1200 shown in FIG. 11*b*. In one embodiment, the reference screen 1200 displays a webpage associated with the selected piece of evidence. In the example shown in FIG. 11*b*, the PubMed™ page associated with the selected piece of evidence is shown. It should be understood that information about the selected piece of evidence may be retrieved from any suitable database of publications or other source of reference material. It should also be understood that the reference screen 1200 may present the evidence data in any suitable format other than a webpage. In the illustrated example, the reference screen 1200 comprises a reference section 1202 providing detailed information (e.g. title, authors, journal, publication date, etc.) about the piece of evidence, such information being retrieved from the PubMed™ database. The reference screen 1200 further comprises a search bar 1204 and matching search option 1206 that enable the user to search the PubMed™ database. The user may return to the indication screen 1000 by selecting a corresponding option 1208.

Figure 12:
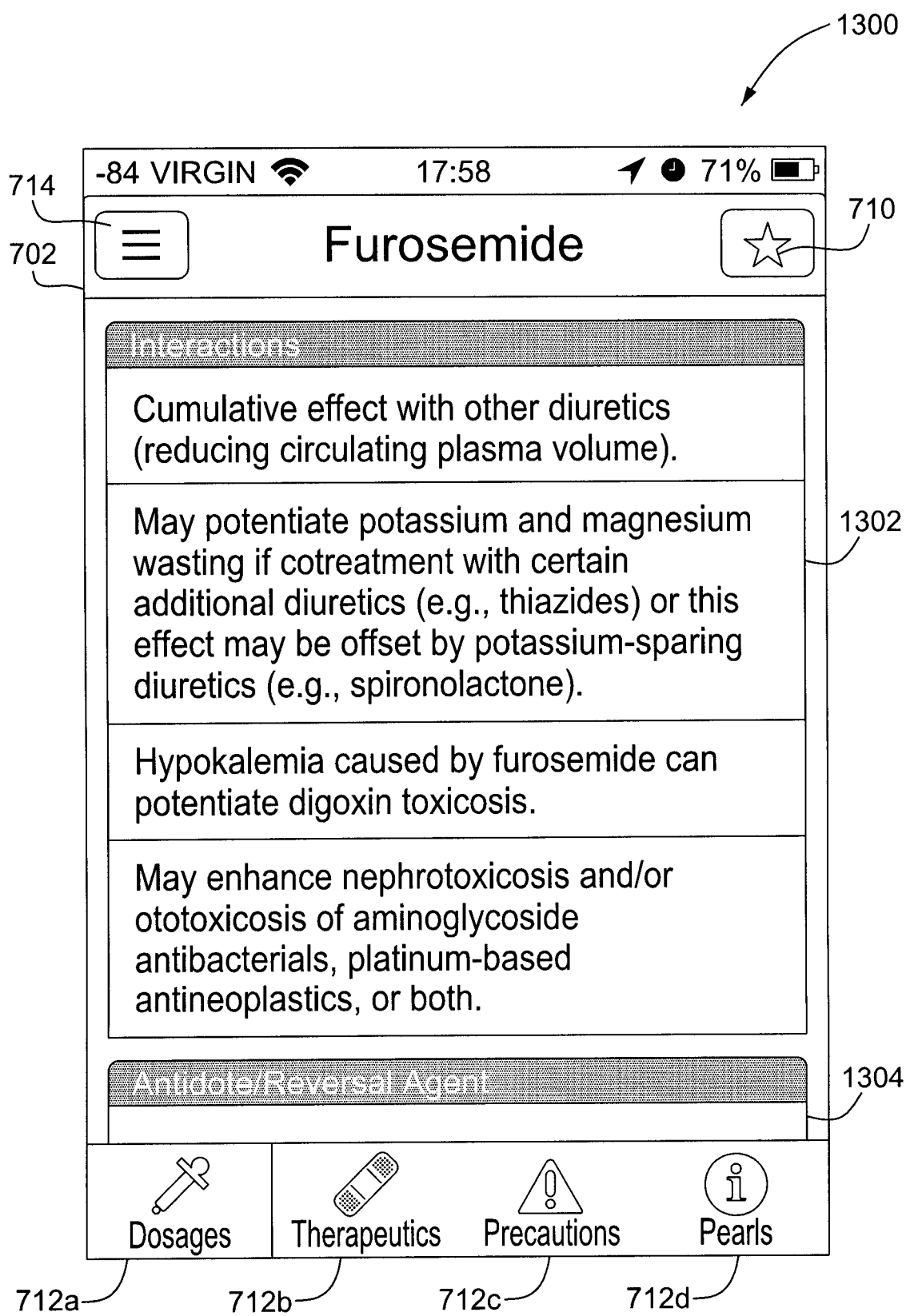
FIG. 12 is a screen capture of a therapeutics screen, in accordance with an illustrative embodiment of the present invention.

Referring now to FIG. 12, upon the user selecting the "Therapeutics" option 712*b*, a therapeutics screen 1300 is presented. The therapeutics screen 1300 provides therapeutic information related to the drug at hand. For instance, information about interactions for the given drug may be presented in an "Interaction" section 1302 of the screen 1300. Information about antidotes or reversal agents for the drug may also be retrieved from memory and presented in an "Antidote/Reversal Agent" section 1304.

Figure 13:
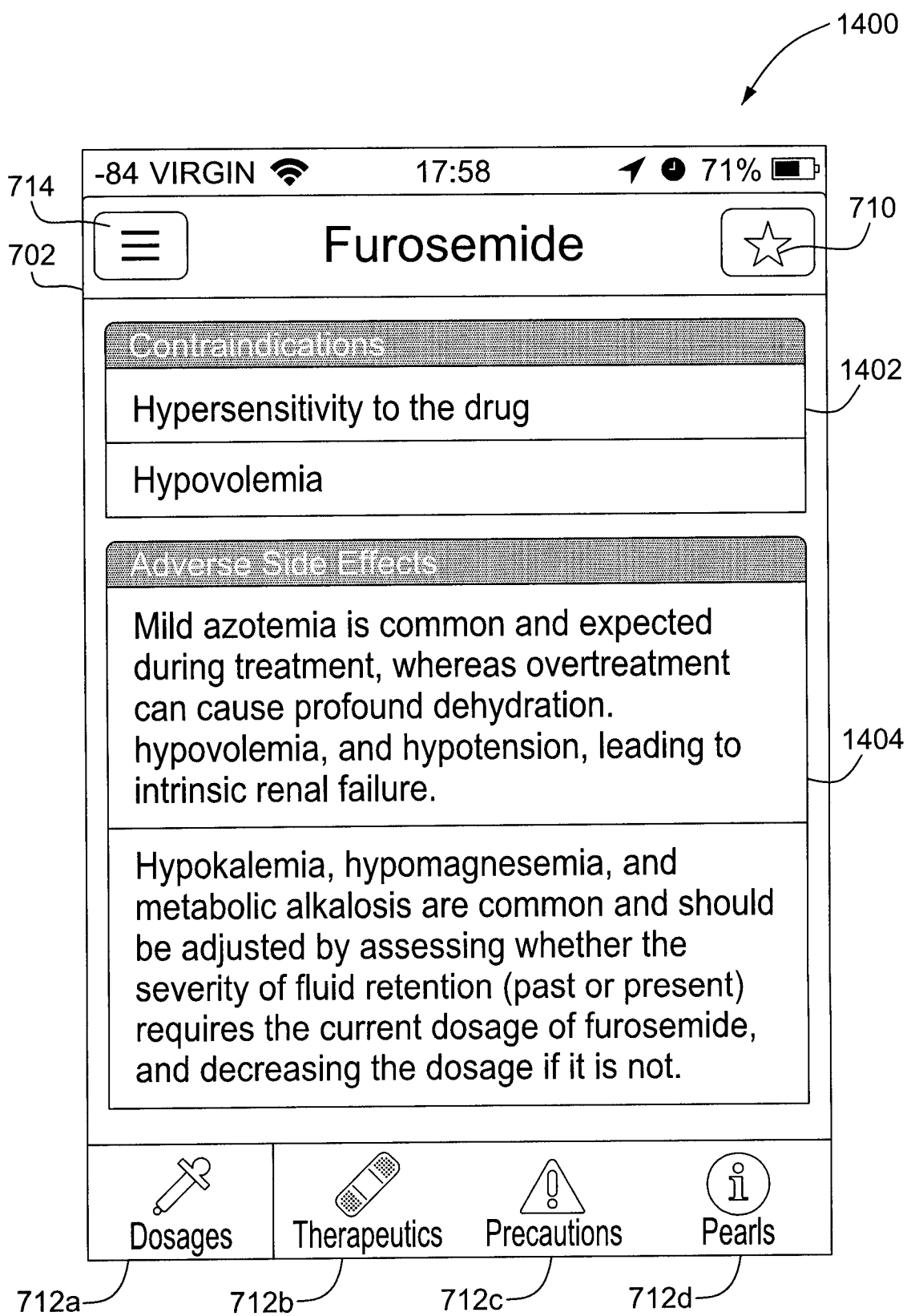
FIG. 13 is a screen capture of a precautions screen, in accordance with an illustrative embodiment of the present invention.

Referring now to FIG. 13, upon the user selecting the "Precautions" option 712*c*, a precautions screen 1400 is presented. The precautions screen 1400 informs the user of precautions to be taken when administering the drug. For instance, information about contraindications for the given drug may be presented in a "Contraindications" section 1402 of the screen 1400. Information about adverse side effects of the drug may also be presented in a corresponding section 1404.

Figure 14:
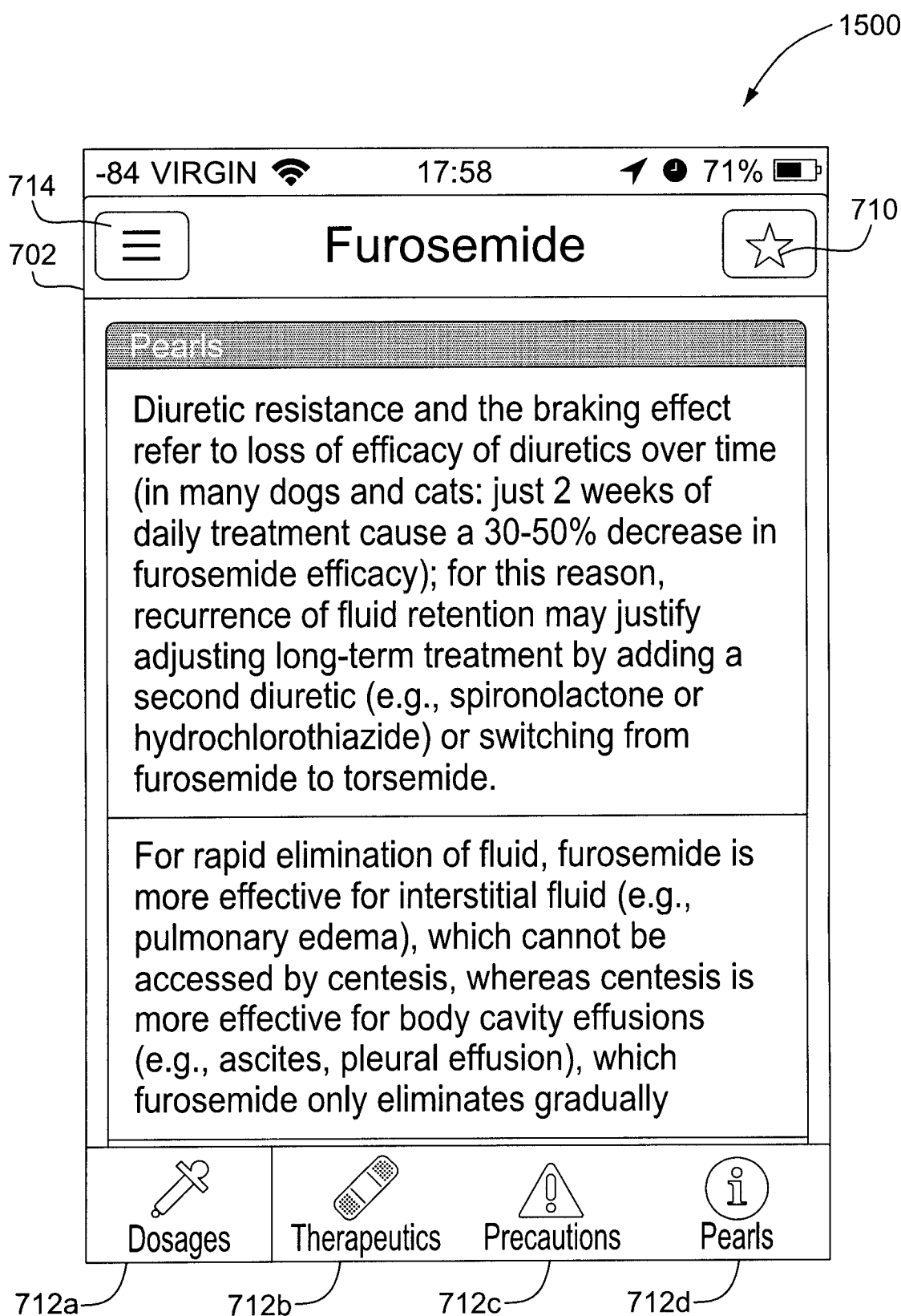
FIG. 14 is a screen capture of a clinical advice screen, in accordance with an illustrative embodiment of the present invention.

Referring now to FIG. 14, upon the user selecting the "Pearls" option 712*d*, a clinical advice screen 1500 is presented. The screen 1500 illustratively presents general tips and advice relevant to the case at hand. For example, tips as to how a given indication is to be treated using the selected drug may be presented. The clinical advice shown in the advice screen 1500 may be obtained from recognized experts.

Figure 15:
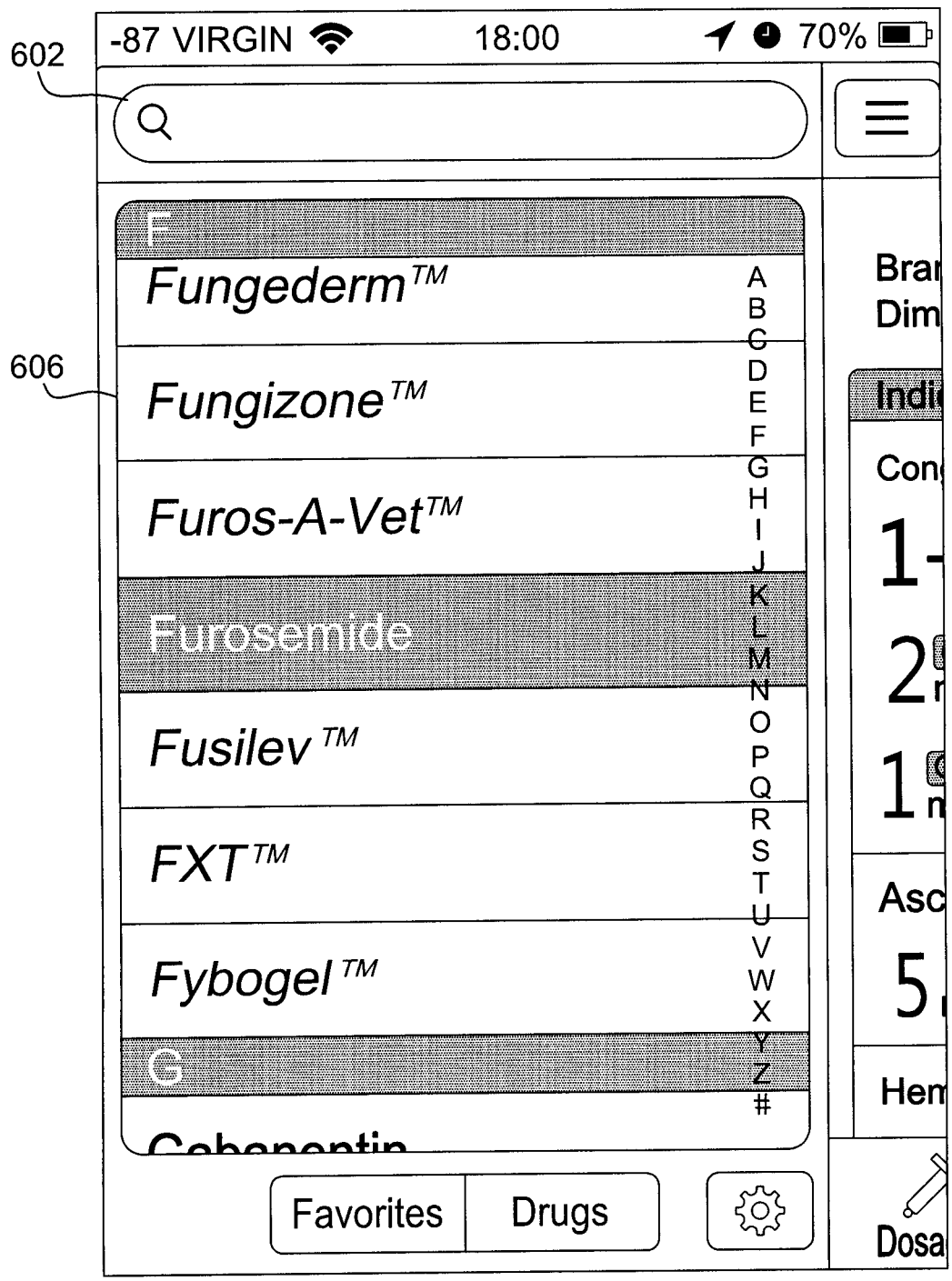
FIG. 15 is a screen capture of a drug list and search screen, in accordance with another illustrative embodiment of the present invention.

Referring now to FIG. 15 in addition to FIG. 14, the user may at any time return to the drug list and search bar by selecting a corresponding list icon 714. Upon selecting the list icon 714, the user is presented with the search bar 602 and drug list 606 discussed above with reference to FIG. 4. The drugs can then be accessed using an alphabetical index provided with the drug list 606 or using the search function of the search bar 602.

Figure 16A:
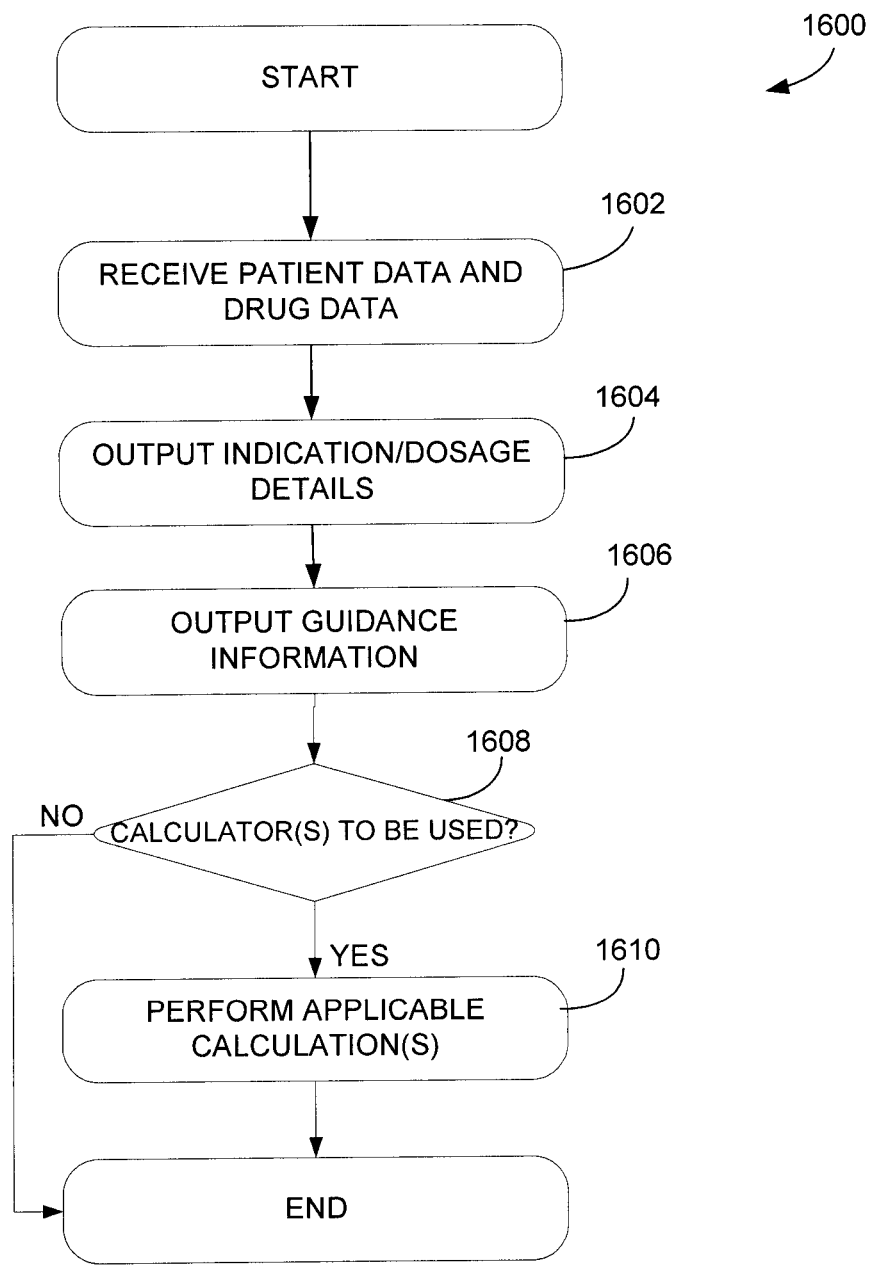
FIG. 16a is a flowchart illustrating an exemplary embodiment of a method for providing drug information, in accordance with an illustrative embodiment of the present invention.

Referring to FIG. 16*a*, a method 1600 for providing drug information in accordance with an illustrative embodiment of the present invention will now be described. The method 1600 comprises receiving at step 1602 patient data and drug data. The drug data may be indicative of a drug for which it is desired to obtain information while the patient data may comprise patient-specific information, such as a weight of a patient to be treated. The next step 1604 may then be to output indication/dosage details for the case at hand on the basis of the received data. Guidance information may further be output at step 1606. The next step 1608 may then be to determine whether calculator(s) are to be used to perform one or more calculations related to the case at hand. If no calculations are to be performed, the method 1600 may end. Otherwise, the method 1600 may flow to the step 1610 of performing calculation(s) applicable to the case at hand.

Figure 16B:
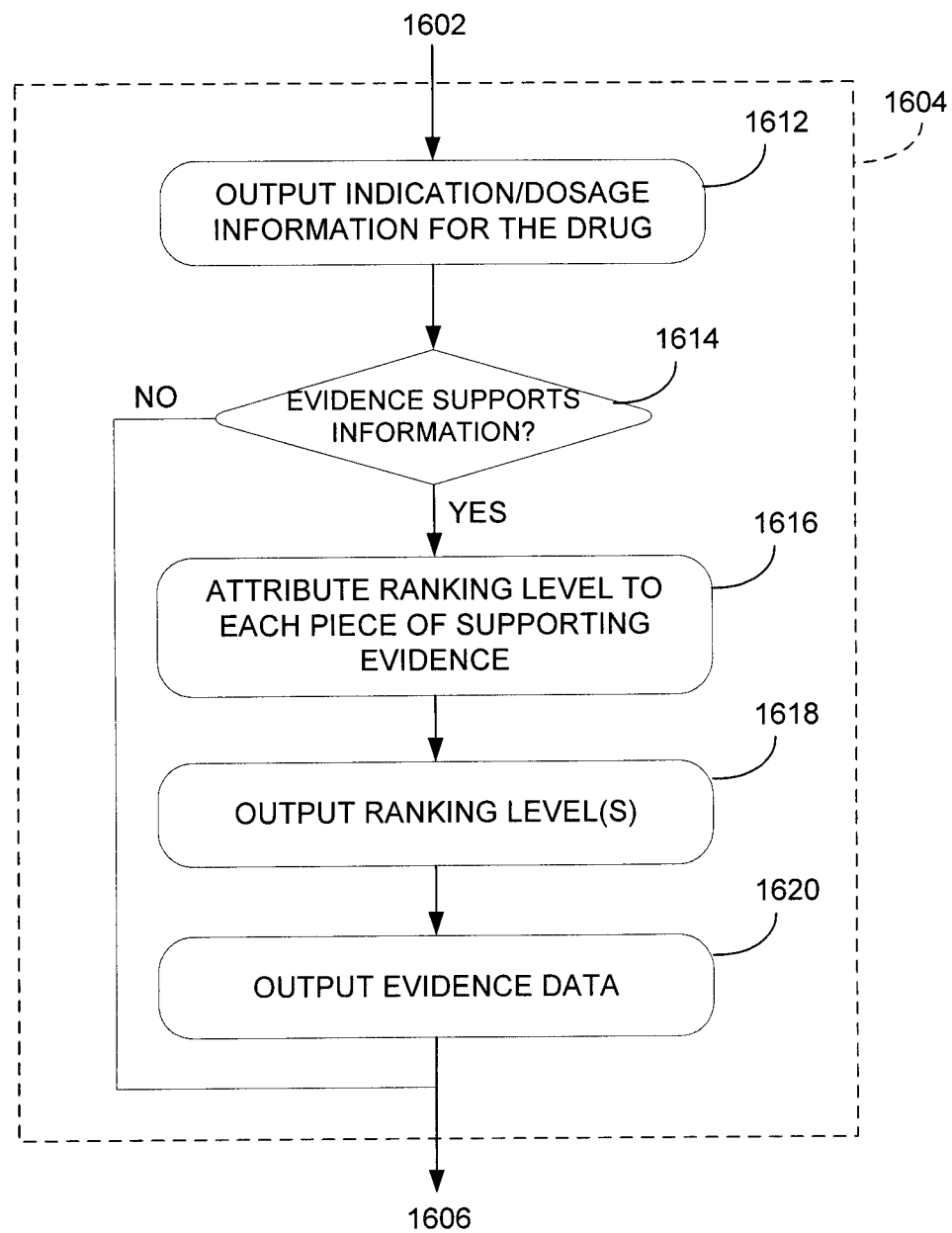
FIG. 16b is a flowchart illustrating the step of FIG. 16a of outputting indication/dosage details.

Referring to FIG. 16*b*, the step 1604 of outputting indication/dosage details illustratively comprises outputting indication/dosage information for the drug at step 1612. Such information may comprise one or more indications the drug is suitable for and dosage(s) for each indication, as discussed above. The next step 1614 may then be to assess whether evidence supports the information output at step 1612. If this is not the case, the next step 1606 may be performed. Otherwise, the next step 1616 may be to attribute a ranking level to each piece of supporting evidence, as discussed above with reference to FIG. 2*c*. It should be understood that step 1616 is optional as the ranking level may be determined by medical expert(s) and received therefrom, as discussed above with reference to the clinical guidance module (reference 208 in FIG. 2*a*). The ranking level(s) attributed to each piece of supporting evidence may then be output at step 1618. The evidence data may also be output at step 1620.

Figure 16C:
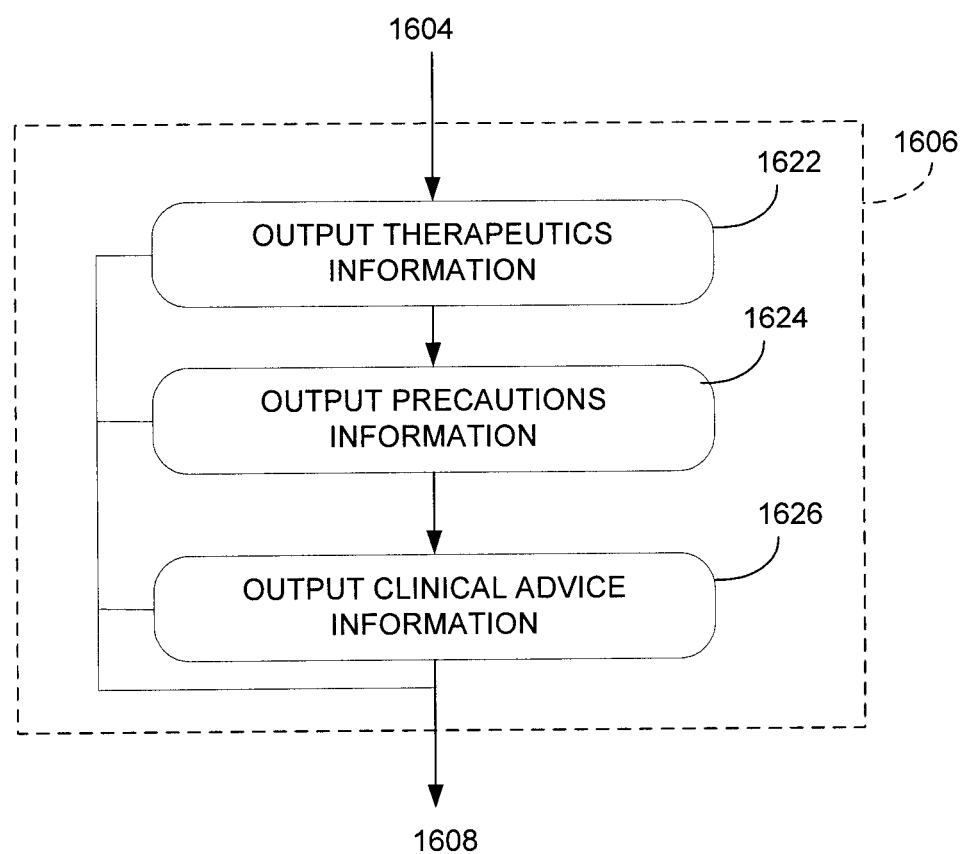
FIG. 16c is a flowchart illustrating the step of FIG. 16a of outputting guidance information.

Referring to FIG. 16*c*, the step 1606 of outputting guidance information illustratively comprises outputting therapeutics information at step 1622, outputting precautions information at step 1624, and outputting clinical advice information at step 1626. It should be understood that at least one of the steps 1622, 1624, and 1626 may be performed.

Figure 16D:
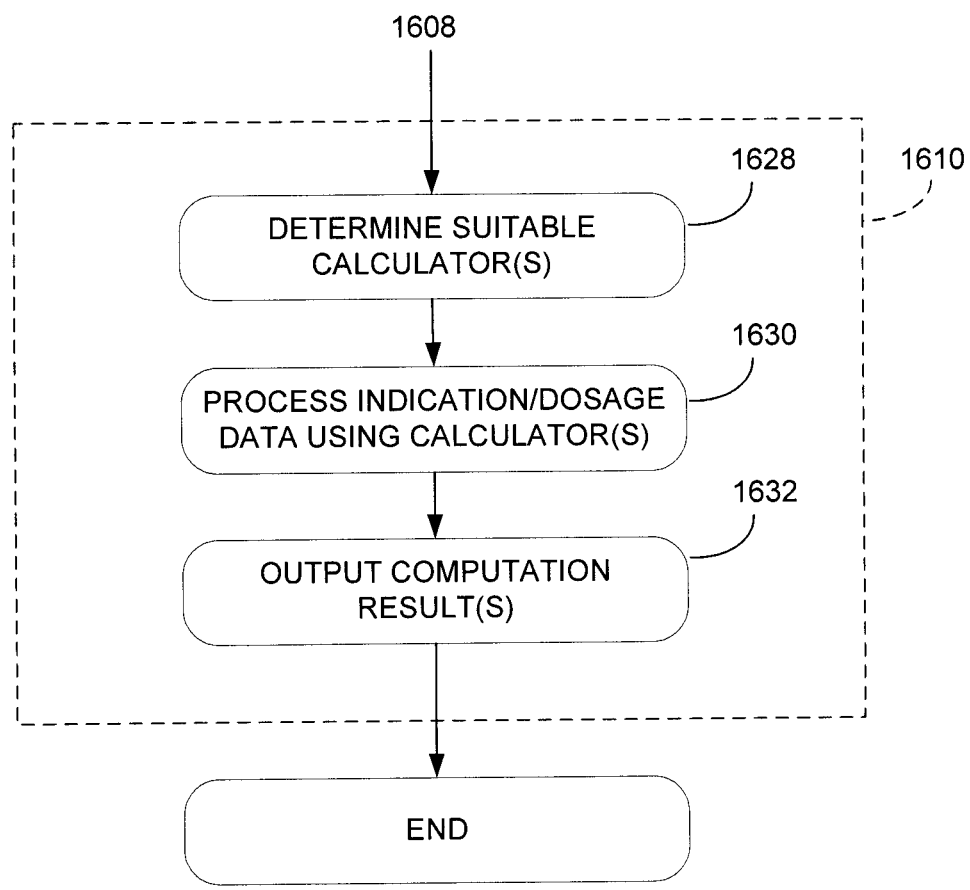
FIG. 16d is a flowchart illustrating the step of FIG. 16a of performing applicable calculation(s).

Referring to FIG. 16*d*, the step 1610 of performing applicable calculation(s) illustratively comprises determining at step 1628 the calculator(s), which are suitable for the case at hand. This may be determined on the basis of the indication/dosage data, as discussed above with reference to FIG. 2*b*. The next step 1630 may then be to process the indication/dosage data using the calculator(s) determined at step 1628 and to output the result(s) of the computation(s) at step 1632.

While illustrated in the block diagrams as groups of discrete components communicating with each other via distinct data signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment.

It should be noted that the present invention can be carried out as a method, can be embodied in a system, and/or on a computer readable medium. The embodiments of the invention described above are intended to be exemplary only. The scope of the invention is therefore intended to be limited solely by the scope of the appended claims.

The invention claimed is:

1. A computer-based drug formulary system, the system comprising:
    a memory populated with drug data identifying a plurality of drugs, and, for each one of the plurality of drugs, at least one indication the drug is prescribed for, a unit dose value of the drug to be administered for treating the at least one indication, and calculation data indicative of at least one calculation applicable for computing a total dosage of the drug to be administered for treating the at least one indication, and evidence-based data indicative of an effectiveness of each one of the plurality of drugs for treating the at least one indication, the evidence-based data supporting the at least one indication for the drug and the total dosage of the drug for treating the at least one indication;
    a processor; and
    at least one application stored in the memory and executable by the processor for:
        presenting to a user an interface for input of input data identifying a selected one of the plurality of drugs;
        receiving the input data via the interface;
        determining the at least one indication the selected drug is prescribed for;
        retrieving from the memory the unit dose value of the selected drug for the at least one indication;
        retrieving from the memory the calculation data for the selected drug and automatically performing the at least one calculation applicable for the selected drug for computing the total dosage of the selected drug for the at least one indication;
        retrieving from the memory the evidence-based data for the selected drug;
        determining a measure of a level of confidence in the evidence-based data for the selected drug comprising, attributing a selected one of a plurality of ranking levels to the evidence-based data for the selected drug and periodically revising the selected ranking level as updated evidence-based data for the selected drug is obtained, the selected ranking level representative of a level of strength of the evidence-based data supporting the at least one indication as determined and the total dosage as computed; and
        outputting, via the interface, for the selected drug, the unit dose value, the total dosage, and the measure of the level of confidence in the evidence-based data for the selected drug, the measure of the level of confidence rendered on the interface as a visual scale indicative of the selected raking level.

2. The system of claim 1, wherein the memory has stored therein one or more attributes for the evidence-based data, the one or more attributes comprising at least one of a type of the evidence-based data, a type of blinding for the evidence-based data, a type of control for the evidence-based data, a randomization for the evidence-based data, a sample group size for the evidence-based data, a number of trials for the evidence-based data, and an assessment of whether an animal signalment is provided in the evidence-based data.

3. The system of claim 2, wherein the memory has stored therein the plurality of ranking levels indicative of the level of confidence in the evidence-based data, each ranking level determined on the basis of the one or more attributes of the evidence-based data and associated with a combination of the one or more attributes, and further wherein the at least one application is executable by the processor for:

receiving the input data indicative of a given one of the at least one indication for which the selected drug is to be administered; and determining the measure of the level of confidence in the evidence-based data indicative of the effectiveness of the selected drug for treating the given indication comprising retrieving the plurality of ranking levels from the memory and correlating the one or more attributes of the evidence-based data for the selected drug with the plurality of ranking levels for attributing the selected ranking level to the evidence-based data for the selected drug.

4. The system of claim 1, wherein the at least one application is executable for outputting the evidence-based data for the selected drug.

5. The system of claim 1, wherein the at least one application is executable by the processor for:

receiving the input data comprising a weight of the patient;

retrieving from the memory the calculation data;

determining from the calculation data that the at least one calculation applicable for computing the total dosage of the selected drug for the given indication comprises multiplying the weight of the patient by the unit dose value of the selected drug for the given indication; and performing the at least one calculation accordingly.

6. The system of claim 1, wherein the memory has stored therein the drug data identifying one or more of the plurality of drugs to be administered by continuous rate infusion, the drug data comprising a recommended continuous rate infusion dosage for each one of the one or more of the plurality of drugs, and further wherein the at least one application is executable by the processor for:

determining from the drug data that the selected drug is among the one or more of the plurality of drugs to be administered by continuous rate infusion;

retrieving the recommended constant rate infusion dosage for the selected drug from the memory;

receiving the input data comprising a weight of the patient, a concentration of the selected drug, a volume of a fluid container for use in administering the selected drug, and a duration of administration of the selected drug;

retrieving from the memory the calculation data;

determining from the calculation data that the at least one calculation comprises computing a total volume of the selected drug to be added to the volume of the fluid container and a drip rate of the fluid container;

performing the at least one calculation on the basis of the retrieved recommended constant rate infusion dosage and the input data; and outputting the computed total volume and drip rate.

7. The system of claim 1, wherein the at least one application is executable by the processor for receiving the input data comprising a height and a weight of the patient, retrieving from the memory the calculation data, determining from the calculation data that the at least one calculation comprises calculating, on the basis of the height and the weight, a body surface area of the patient and computing the total dosage for the selected drug on the basis of the calculated body surface area and the unit dose value of the selected drug for the given indication, and performing the at least one calculation accordingly.

8. The system of claim 1, wherein the memory has stored therein the drug data comprising one or more attributes of the plurality of drugs, the one or more attributes comprising, for each one of the plurality of drugs, at least one of a brand name of the drug, a generic name of the drug, a therapeutic class of the drug, a regional availability of the drug, a rate of administration of the drug, a mode of administration of the drug, a type of condition the drug is indicated for, advice for treating the condition using the drug, one or more contraindications of the drug, one or more effects from administration of the drug, one or more combination treatments to be used with the drug, one or more reversal agents for the drug, and one or more animal species the drug is indicated for treating, and further wherein the at least one application is executable by the processor for retrieving at least one of the one or more attributes for the selected drug from the memory and outputting the retrieved at least one of the one or more attributes.

9. A computer-implemented method for generating a treatment protocol, the method comprising:

presenting to a user an interface for input of input data identifying a selected one of the plurality of drugs;

receiving the input data via the interface;

determining at least one indication the selected drug is prescribed for;

retrieving a unit dose value of the selected drug for the at least one indication from a memory populated with drug data identifying the plurality of drugs, and, for each one of the plurality of drugs, the at least one indication the drug is prescribed for, the unit dose value of the drug to be administered for treating each of the at least one indication, and calculation data indicative of at least one calculation applicable for computing a total dosage of the drug to be administered for treating the at least one indication, and evidence-based data indicative of an effectiveness of each one of the plurality of drugs for treating the at least one indication, the evidence-based data supporting the at least one indication for the drug and the total dosage of the drug for treating the at least one indication;

retrieving from the memory the calculation data for the selected drug and automatically performing the at least one calculation applicable for the selected drug for computing the total dosage of the selected drug for the at least one indication;

retrieving from the memory the evidence-based data for the selected drug;

determining a measure of a level of confidence in the evidence-based data for the selected drug comprising, attributing a selected one of a plurality of ranking levels to the evidence-based data for the selected drug and periodically revising the selected ranking level as updated evidence-based data for the selected drug is obtained, the selected ranking level representative of a level of strength of the evidence-based data supporting the at least one indication as determined and the total dosage as computed; and outputting, via the interface, for the selected drug, the unit dose value, the total dosage, and the measure of the level of confidence in the evidence-based data for the selected drug, the measure of the level of confidence rendered on the interface as a visual scale indicative of the selected raking level.

10. The method of claim 9, further comprising:

receiving the input data indicative of a given one of the at least one indication for which the selected drug is to be administered; and determining the measure of the level of confidence in the evidence-based data indicative of the effectiveness of the selected drug for treating the given indication comprising:
retrieving the plurality of ranking levels from the memory, the memory having stored therein one or more attributes for the evidence-based data and the plurality of ranking levels indicative of the level of confidence in the evidence-based data, each ranking level determined on the basis of the one or more attributes of the evidence-based data and associated with a combination of the one or more attributes, and
correlating the one or more attributes of the evidence-based data for the selected drug with the plurality of ranking levels for attributing the selected ranking level to the evidence-based data for the selected drug.

11. The method of claim 9, further comprising outputting the evidence-based data for the selected drug.

12. The method of claim 9, further comprising:
receiving the input data comprising a weight of the patient;
retrieving the calculation data from the memory;
determining from the calculation data that the at least one calculation applicable for computing the total dosage of the selected drug for the given indication comprises multiplying the weight of the patient by the unit dose value of the selected drug for the given indication; and
performing the at least one calculation accordingly.

13. The method of claim 9, further comprising:
determining from the drug data that the selected drug is among one or more of the plurality of drugs to be administered by continuous rate infusion;
retrieving a recommended constant rate infusion dosage for the selected drug from the memory;
receiving the input data comprising a weight of the patient, a concentration of the selected drug, a volume of a fluid container for use in administering the selected drug, and a duration of administration of the selected drug;
retrieving from the calculation data the memory;
determining from the calculation data that the at least one calculation comprises computing a total volume of the selected drug to be added to the volume of the fluid container and a drip rate of the fluid container;
performing the at least one calculation on the basis of the retrieved recommended constant rate infusion dosage and the input data; and
outputting the computed total volume and drip rate.

14. The method of claim 9, further comprising receiving the input data comprising a height and a weight of the patient, retrieving the calculation data from the memory, determining from the calculation data that the at least one calculation comprises calculating, on the basis of the height and the weight, a body surface area of the patient and computing the total dosage for the selected drug on the basis of the calculated body surface area and the unit dose value of the selected drug for the given indication, and performing the at least one calculation accordingly.

15. The method of claim 9, further comprising retrieving at least one of one or more attributes for the selected drug from the memory and outputting the retrieved at least one of the one or more attributes, the one or more attributes comprising, for each one of the plurality of drugs, at least one of a brand name of the drug, a generic name of the drug, a therapeutic class of the drug, a regional availability of the drug, a rate of administration of the drug, a mode of administration of the drug, a type of condition the drug is indicated for, advice for treating the condition using the drug, one or more contraindications of the drug, one or more effects from administration of the drug, one or more combination treatments to be used with the drug, one or more reversal agents for the drug, and one or more animal species the drug is indicated for treating.

16. A computer readable medium having stored thereon program code executable by a processor for, the program code executable for:
presenting to a user an interface for input of input data identifying a selected one of the plurality of drugs;
receiving the input data via the interface;
determining at least one indication the selected drug is prescribed for;
retrieving a unit dose value of the selected drug for the at least one indication from a memory populated with drug data identifying the plurality of drugs, and, for each one of the plurality of drugs, the at least one indication the drug is prescribed for, the unit dose value of the drug to be administered for treating each of the at least one indication, and calculation data indicative of at least one calculation applicable for computing a total dosage of the drug to be administered for treating the at least one indication, and evidence-based data indicative of an effectiveness of each one of the plurality of drugs for treating the at least one indication, the evidence-based data supporting the at least one indication for the drug and the total dosage of the drug for treating the at least one indication;
retrieving from the memory the calculation data for the selected drug and automatically performing the at least one calculation applicable for the selected drug for computing the total dosage of the selected drug for the at least one indication;
retrieving from the memory the evidence-based data for the selected drug;
determining a measure of a level of confidence in the evidence-based data for the selected drug comprising, attributing a selected one of a plurality of ranking levels to the evidence-based data for the selected drug and periodically revising the selected ranking level as updated evidence-based data for the selected drug is obtained, the selected ranking level representative of a level of strength of the evidence-based data supporting the at least one indication as determined and the total dosage as computed; and
outputting, via the interface, for the selected drug, the unit dose value, the total dosage, and the measure of the level of confidence in the evidence-based data for the selected drug, the measure of the level of confidence rendered on the interface as a visual scale indicative of the selected raking level.

* * * * *